US012593991B2

(12) United States Patent
Zhang et al.

(10) Patent No.: US 12,593,991 B2
(45) Date of Patent: Apr. 7, 2026

(54) METHOD AND A DEVICE FOR CALIBRATING A BLOOD PRESSURE ESTIMATION MODEL FOR DETERMINING TONOARTERIOGRAM SIGNALS

(71) Applicant: Hong Kong Centre for Cerebro-Cardiovascular Health Engineering Limited, Hong Kong (CN)

(72) Inventors: Yuanting Zhang, Hong Kong (CN); Ting Xiang, Hong Kong (CN); Zijun Liu, Hong Kong (CN); Nan Ji, Hong Kong (CN)

( * ) Notice: Subject to any disclaimer, the term of this patent is extended or adjusted under 35 U.S.C. 154(b) by 715 days.

(21) Appl. No.: 17/976,881

(22) Filed: Oct. 31, 2022

(65) Prior Publication Data

US 2023/0404416 A1 Dec. 21, 2023

(30) Foreign Application Priority Data

Jun. 15, 2022 (CN) .......................... 202210680498.5

(51) Int. Cl.
*A61B 5/021* (2006.01)
*A61B 5/00* (2006.01)

(52) U.S. Cl.
CPC ........ *A61B 5/02108* (2013.01); *A61B 5/7235* (2013.01); *A61B 5/02116* (2013.01)

(58) Field of Classification Search
CPC .............. A61B 5/02108; A61B 5/7235; A61B 5/02116; A61B 5/7203; A61B 5/725;
(Continued)

(56) References Cited

U.S. PATENT DOCUMENTS 7,641,614 B2    1/2010  Asada et al.
7,674,231 B2    3/2010  McCombie et al.
(Continued)

FOREIGN PATENT DOCUMENTS

CN        1692874 A    11/2005
CN      101773387 A    12/2011
CN      106510666 A     3/2017

OTHER PUBLICATIONS

CN106510666 English Translation, Espacenet Machine Translation, Nov. 1, 2022, European Patent Office (EPO), Munich, Germany.
(Continued)

*Primary Examiner* — Tse W Chen
*Assistant Examiner* — Joseph A Tombers
(74) *Attorney, Agent, or Firm* — Nevin Carmichael IP

(57) ABSTRACT

The present invention provides a method and a device for calibrating a blood pressure estimation model for determining tonoarteriogram (TAG) signals, which relates to a cross field between biomedicine and scientific engineering. The method comprises: after applying a first pressure to a first preset location, determining individual pulse transit time (PTT) of a respective pulse wave at a preset region during a preset movement process in a plurality of preset time periods; for each of the preset time period, acquiring a first pressure at the respective first moment of time and a first height difference of the first preset location relative to a heart location; acquiring a second pressure according to the first pressure at all of the first moment of time; determining a sample blood pressure information within the preset time period according to the second pressure and the first height difference to calibrate the blood pressure estimation model, and obtaining a continuous beat-to-beat blood pressure information according to the blood pressure estimation model, obtaining TAG signals according to the beat-to-beat blood pressure information and a target PPG signal. The present invention calibrates the blood pressure estimation model without the need of a cuff-type blood pressure measurement device, and a high-precision TAG signals can be obtained.

13 Claims, 14 Drawing Sheets

◇  Accelerometer

▨  Pressure sensor

▨  PPG sensor

LED
PD

LEDs

(58) Field of Classification Search
CPC ........ A61B 2560/0223; A61B 5/02125; A61B 5/02225; G06F 17/18
See application file for complete search history.

(56) References Cited

U.S. PATENT DOCUMENTS

| 8,313,439 | B2 | 11/2012 | McCombie et al. | |
| 2008/0039731 | A1* | 2/2008 | McCombie | A61B 5/02255 |
| | | | | 600/485 |
| 2010/0168589 | A1* | 7/2010 | Banet | A61B 5/02125 |
| | | | | 600/490 |
| 2011/0105918 | A1* | 5/2011 | Fortin | A61B 5/7203 |
| | | | | 600/493 |
| 2019/0008399 | A1* | 1/2019 | Mukkamala | A61B 5/0261 |
| 2021/0096657 | A1 | 4/2021 | D'Amone et al. | |
| 2021/0169345 | A1 | 6/2021 | Wasson et al. | |
| 2021/0378529 | A1* | 12/2021 | Colburn | A61B 5/681 |

OTHER PUBLICATIONS

CN1692874 English Translation, Espacenet Machine Translation, Nov. 1, 2022, European Patent Office (EPO), Munich, Germany.
CN101773387 English Translation, Espacenet Machine Translation, Nov. 1, 2022, European Patent Office (EPO). Munich, Germany.

* cited by examiner

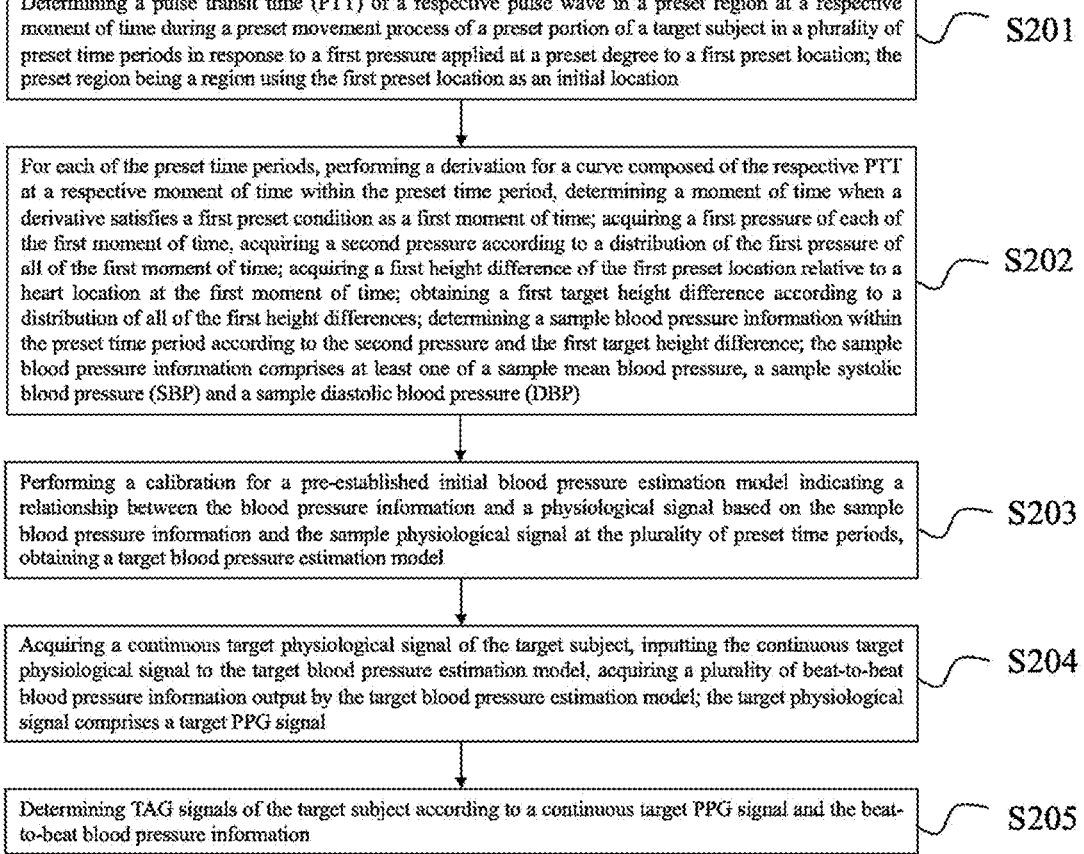

Determining a pulse transit time (PTT) of a respective pulse wave in a preset region at a respective moment of time during a preset movement process of a preset portion of a target subject in a plurality of preset time periods in response to a first pressure applied at a preset degree to a first preset location; the preset region being a region using the first preset location as an initial location          S201

For each of the preset time periods, performing a derivation for a curve composed of the respective PTT at a respective moment of time within the preset time period, determining a moment of time when a derivative satisfies a first preset condition as a first moment of time; acquiring a first pressure of each of the first moment of time, acquiring a second pressure according to a distribution of the first pressure of all of the first moment of time; acquiring a first height difference of the first preset location relative to a heart location at the first moment of time; obtaining a first target height difference according to a distribution of all of the first height differences; determining a sample blood pressure information within the preset time period according to the second pressure and the first target height difference; the sample blood pressure information comprises at least one of a sample mean blood pressure, a sample systolic blood pressure (SBP) and a sample diastolic blood pressure (DBP)          S202

Performing a calibration for a pre-established initial blood pressure estimation model indicating a relationship between the blood pressure information and a physiological signal based on the sample blood pressure information and the sample physiological signal at the plurality of preset time periods, obtaining a target blood pressure estimation model          S203

Acquiring a continuous target physiological signal of the target subject, inputting the continuous target physiological signal to the target blood pressure estimation model, acquiring a plurality of beat-to-beat blood pressure information output by the target blood pressure estimation model; the target physiological signal comprises a target PPG signal          S204

Determining TAG signals of the target subject according to a continuous target PPG signal and the beat-to-beat blood pressure information          S205

FIG. 2 semi-encapsulated and fully
encapsulated inflatable cuff

Four-layer design
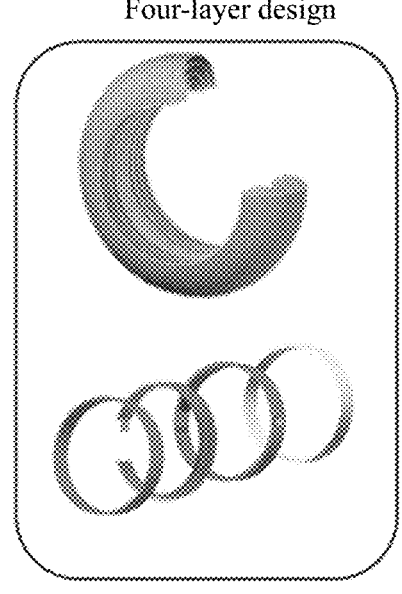
FIG. 5a
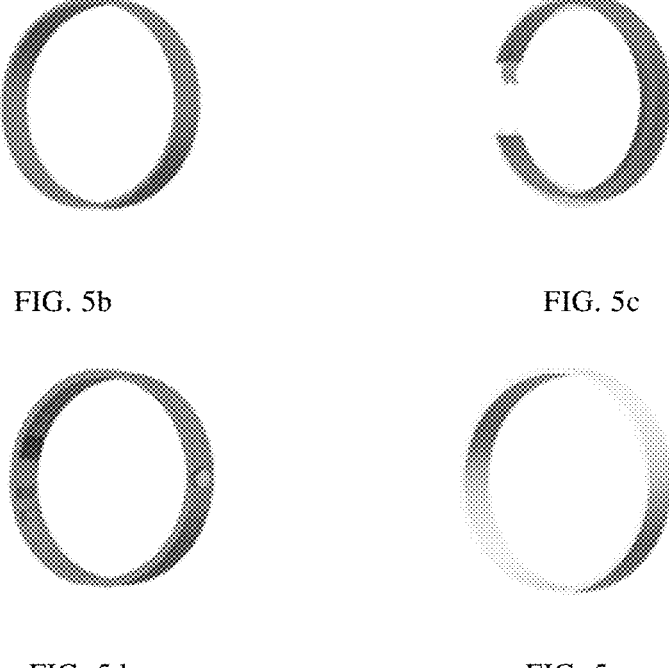
FIG. 5b
FIG. 5c
FIG. 5d
FIG. 5e

METHOD AND A DEVICE FOR CALIBRATING A BLOOD PRESSURE ESTIMATION MODEL FOR DETERMINING TONOARTERIOGRAM SIGNALS

FIELD OF THE INVENTION

The present invention relates to a cross field between biomedical and scientific engineering, specifically, this application relates to provides a method and a device for calibrating a blood pressure estimation model for determining tonoarteriogram (TAG) signals.

BACKGROUND OF THE INVENTION

Cardiovascular disease (CVD) is the leading cause of death and disability worldwide and is the number one killer. Among the multiple mortality factors of cardiovascular disease, hypertension ranks first and is the most critical risk factor; therefore, it is essential to perform blood pressure measurements in daily life.

Existing devices for measuring blood pressure are wearable blood pressure measurement devices, which measure blood pressure through a blood model, and the relationship between blood pressure information and physiological signals on the surface of this blood pressure estimation model; after the blood model is constructed, the wearable blood pressure measurement device inputs the collected physiological signals into the corresponding blood pressure estimation model to obtain blood pressure information. However, most blood pressure estimation models have related calibration parameters, which are unknown constant parameters. The process of determining these parameters is called the calibration process of the blood pressure model. It is evident that the whole calibration process requires the use of additional cuff blood pressure measurement devices, and it is necessary to manually bring multiple single samples of blood pressure measured by the cuff blood pressure measurement devices into the blood pressure estimation model to obtain the unknown constant parameters, which is a tedious and complicated process.

OBJECTS OF THE INVENTION

An object of the present invention is to provide a method and a device for calibrating a blood pressure estimation model for determining tonoarteriogram (TAG) signals.

The above object is met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

The present invention provides a method, a device, electronic device, computer-readable storage medium, and computer program product for calibrating a blood pressure estimation model for determining TAG signals, which can solve the problem of needing to calibrate a blood pressure estimation model with the help of sample blood pressure measured by an additional cuff blood pressure measurement device. The described technical solution is as follows.

According to a first aspect of embodiments of the present application, there is provided a method of calibrating a blood pressure estimation model for determining a TAG signal, the method comprising: determining a PTT of a respective pulse wave in a preset region at a respective moment of time during a preset movement process of a preset portion of a target subject in a plurality of preset time periods in response to a first pressure applied at a preset degree to a first preset location; the preset region being a region using the first preset location as an initial location; for each of the preset time periods, performing a derivation for a curve composed of the respective PTT at a respective moment of time within the preset time period, determining a moment of time when a derivative satisfies a first preset condition as a first moment of time; acquiring a first pressure of each of the first moment of time, acquiring a second pressure according to a distribution of the first pressure of all of the first moment of time; acquiring a first height difference of the first preset location relative to a heart location at the first moment of time; obtaining a first target height difference according to a distribution of all of the first height differences; determining a sample blood pressure information within the preset time period according to the second pressure and the first target height difference; the sample blood pressure information comprises at least one of a sample mean blood pressure, a sample SBP and a sample DBP; performing a calibration for a pre-established initial blood pressure estimation model indicating a relationship between the blood pressure information and a physiological signal based on the sample blood pressure information and the sample physiological signal at the plurality of preset time periods, obtaining a target blood pressure estimation model; acquiring a continuous target physiological signal of the target subject, inputting the continuous target physiological signal to the target blood pressure estimation model, acquiring a plurality of beat-to-beat (B2B) blood pressure information output by the target blood pressure estimation model; the target physiological signal comprises a target PPG signal; determining TAG signals of the target subject according to a continuous target PPG signal and the beat-to-beat blood pressure information.

In one possible implementation, the step of determining the sample blood pressure information within the preset time period according to the second pressure and the first target height difference, further comprises: determining the respective moment of time when an oscillation amplitude of a pulse wave is at a maximum value determined via a sample PPG signal at the first preset location as a second moment of time; acquiring the first pressure of the respective second moment of time, acquiring a third pressure according to a distribution of the first pressure at all of the second moment of time; acquiring a second height difference of the first preset location at the respective second moment of time relative to the heart location, obtaining a second target height difference according to a distribution of all of the second height differences; determining a fourth pressure as a mean value of the second pressure and the third pressure; taking a mean value of the first target height difference and the second target height difference as a third target height difference; determining the sample blood pressure information within the preset time period according to the fourth pressure and the third target height difference.

In one possible implementation, the step of determining the TAG signals of the target subject according to the continuous target PPG signal and the beat-to-beat blood pressure information comprises: determining a pre-established transfer function between the target PPG signal and the blood pressure information, inputting the beat-to-beat blood pressure information and the continuous PPG signal into the transfer function, obtaining the TAG signals output from the transfer function.

In one possible implementation, the step of determining the sample blood pressure information within each of the preset time periods according to the second pressure and the first target height difference comprising: acquiring a blood density of the target subject, determining a first blood static pressure at the first preset location according to the blood density and the first target height difference; determining the sample blood pressure information within each of the preset time periods according to the second pressure and the first blood static pressure.

In one possible implementation, determining the sample blood pressure information for each predetermined time period based on the second pressure as well as the first blood static pressure, the step of determining the sample blood pressure information within each of the preset time periods according to the second pressure and the first blood static pressure comprises: taking a sum of the second pressure and the first blood static pressure as the sample mean blood pressure; determining the blood pressure at a first preset ratio of a rising edge of the derivative as a first SBP; taking a sum of the first SBP and the first blood static pressure as the sample SBP; determining the blood pressure at a second preset ratio of a falling edge of the derivative as a first DBP; taking a sum of the first DBP and the first blood static blood pressure as the sample DBP.

In one possible implementation, the sample blood pressure information for a predetermined time period is determined based on the fourth pressure as well as the third target height difference, wherein the step of determining the sample blood pressure information within the preset time period according to the fourth pressure and the third target height difference comprises: acquiring a blood density of the target subject, determining a second blood static pressure at the first preset location according to the blood density and the third target height difference; determining the sample blood pressure information within the preset time period according to the fourth pressure and the second blood static pressure.

In one possible implementation, the sample blood pressure information for a predetermined time period is determined based on the fourth pressure as well as the second blood static pressure, wherein the step of determining the sample blood pressure information within the preset time period according to the fourth pressure and the second blood static pressure comprises: taking a sum of the fourth pressure and the second blood static pressure as the sample mean blood pressure; determining an envelope of an oscillatory wave of the sample PPG signal at the first preset location; determining the blood pressure at a third preset ratio of a rising edge of the envelope as a second blood pressure; taking a sum of the second SBP and the second blood static pressure as a sample SBP; determining the blood pressure at a fourth preset ratio of a falling edge of the envelope as a second DBP; taking a sum of the second DBP and the second blood static pressure as a sample DBP.

In one possible implementation, a pre-determined degree of first pressure is applied to the first pre-determined position, the step of applying the first pressure at the preset degree to the first preset location comprises: at the first preset location, applying the first pressure at the preset degree by adjusting a diameter or a contact pressure of a target ring-shaped device.

In one possible implementation, the target ring-shaped device is worn at the first preset location; the first preset location being a distal end of a finger; the preset region further comprises a second preset location, if the second preset location being a proximal end of the finger, a non-adjustable and PPG signal collectable ring-shaped device is worn at the second preset location; if the second preset location being other location not at a proximal end of the finger, a corresponding PPG signal collectable external electronic apparatus is worn at the second preset location.

In one possible implementation, a filtering method of the sample PPG signal or the target PPG signal is as follow: acquiring an original PPG signal of a plurality of channels; for the original PPG signal of any one of the channels, extracting a target component from the PPG signal by integrating a constrained independent component analysis, an adaptive filtering, and a baseless source quantity assumption method, and inputting the target component into an adaptive filter to instruct the adaptive filter to perform recovery of the PPG signal according to the target component.

In one possible implementation, after determining the TAG signal of the target object based on the continuous target PPG signal and the beat-to-beat blood pressure information, after the step of determining TAG signals of the target subject according to a continuous target PPG signal and the beat-to-beat blood pressure information, further comprises: transmitting the TAG signals to an external display apparatus to instruct the external display apparatus to display the TAG signal.

According to a second aspect of embodiments of the present application, there is provided a calibration device of a blood pressure estimation model for determining TAG signals, comprising: a PTT determining module for determining a PTT of a respective pulse wave at a respective moment of time in a preset region during a preset movement process of a preset portion of a target subject in a plurality of preset time periods in response to a first pressure applied at a preset degree to a first preset location; the preset region is a region of an initial location of the first preset location; a sample blood pressure information determining module for performing a derivation for a curve composed of the respective PTT at a respective moment of time within each of the preset time period, determining a moment of time when a derivative satisfies a first preset condition as a first moment of time; acquiring a first pressure of each of the first moment of time, acquiring a second pressure according to a distribution of the first pressure of all the first moment of time; acquiring a first height difference of the first preset location at the first moment of time relative to a heart location; obtaining a first target height difference according to a distribution of all the first height differences; determining a sample blood pressure information within the preset time period according to the second pressure and the first target height difference; the sample blood pressure information comprises at least one of a sample mean blood pressure, a sample SBP and a sample DBP; a blood pressure estimation model obtaining module for performing a calibration for a pre-established initial blood pressure estimation model indicating a relationship between the blood pressure information and a physiological signal based on the sample blood pressure information and the sample physiological signal of the plurality of preset time periods, obtaining a target blood pressure estimation model; a beat-to-beat blood pressure information determining module for acquiring a continuous target physiological signal of the target subject at the first preset location, inputting the continuous target physiological signal to a pre-established target blood pressure estimation model to acquire a plurality of beat-to-beat blood pressure information output by the target blood pressure estimation model; the target physiological signal comprises a target PPG signal; TAG signals determining module for determining TAG signals of the target subject according to a continuous target PPG signal and the beat-to-beat blood pressure information.

According to a third aspect of an embodiment of the present application, there is provided an electronic device comprising a memory, a processor and a computer program stored on the memory, the processor executing the program to implement the steps of the method as provided in the first aspect. An electronic apparatus, comprising: a memory, a processor and a computer program stored in the memory, wherein the processor executes the computer program to implement the method steps of the first aspect.

According to a fourth aspect of embodiments of the present application, there is provided a computer readable storage medium having a computer program stored thereon, which computer program when executed by a processor implements the steps of the method as provided in the first aspect. A computer-readable storage medium on which a computer program is stored, wherein, when the computer program is executed by a processor, implements the method steps of the first aspect.

According to a fifth aspect of an embodiment of the present application, there is provided a computer program product comprising computer instructions that are stored in a computer readable storage medium, and when a processor of a computer device reads the computer instructions from the computer readable storage medium, the processor executes the computer instructions such that the computer device performs steps that implement a method as provided in the first aspect.

The present application embodiment determines the PTT of each pulse wave in the preset region at each moment during the preset action of the preset part of the target object in a plurality of preset time periods by responding to applying a preset degree of first pressure to the first preset position; the preset region is the region starting from the first preset position; for each preset time period, the PTT of each pulse wave at each moment in the preset time period is determined as the first moment; for each first moment, the curve composed of the first pressure for each predetermined time period, the derivative of the curve composed of the PTTs for each moment of the predetermined time period is determined, and the moment whose derivative meets the first predetermined condition is the first moment; for each first moment, the first pressure of the first moment and the first height difference of the first predetermined position at the first moment with respect to the heart position are obtained; based on the distribution of the first pressure of all the first moments, the second pressure is obtained; based on the second pressure and the first height difference, the sample blood pressure information of the predetermined time period is determined; the sample blood pressure information of the sample blood pressure information during the predetermined time period; the sample blood pressure information includes at least one of sample mean blood pressure, sample SBP, and sample DBP; based on the sample blood pressure information and sample physiological signals for multiple predetermined time periods, the initial blood pressure estimation model, which was established in advance to indicate the relationship between the blood pressure information and the physiological signals, is calibrated to obtain a target blood pressure estimation model; a continuous target physiological signal of the target subject is obtained, and the continuous target physiological signal of the target object, inputting the continuous target physiological signal to the target blood pressure estimation model, and obtaining a plurality of beat-to-beat blood pressure information output by the target blood pressure estimation model; the target physiological signal includes a target PPG signal; and determining a TAG signal of the target object based on the continuous target PPG signal and the beat-to-beat blood pressure information. The application embodiment can calibrate the initial blood pressure estimation model by using the sample blood pressure information at the first predetermined position to obtain the target blood pressure estimation model, and the initial blood pressure estimation model can be calibrated without the need for additional sample blood pressure information measured by a cuff blood pressure measurement device, TAG signal from the target blood pressure model.

BRIEF DESCRIPTION OF THE DRAWINGS

To illustrate the technical solutions more clearly in the embodiments of the present application, the following is a brief description of the accompanying drawings that need to be used in the description of the embodiments of the present application.

FIG. 2 shows a schematic diagram of a calibration method for determining a blood pressure estimation model for TAG signals provided in an embodiment of the present application;

FIG. 5a shows a schematic diagram of the corresponding four-layer structure of the target finger ring device;

FIG. 5b shows a schematic diagram of the outermost layer of the four-layer structure of the target finger ring device;

FIG. 5c shows a schematic diagram of the third layer of the four-layer structure of the target finger ring device;

FIG. 5d shows a schematic diagram of the second layer of the four-layer structure of the target finger ring device;

FIG. 5e shows a schematic diagram of the innermost layer of the four-layer structure of the target finger ring device;

DESCRIPTION OF PREFERRED EMBODIMENTS

Figure 1:
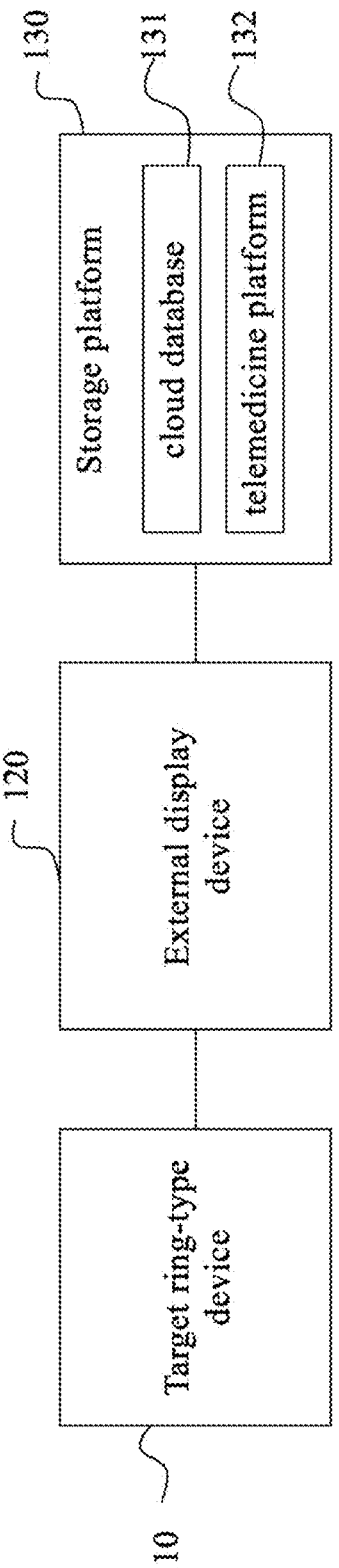
FIG. 1 shows a schematic diagram of the system architecture provided by embodiments of the present application for implementing TAG signals measured and displayed by a blood pressure estimation model.

Embodiments of the present invention are described in connection with the following figures in the present invention. It should be understood that the embodiments set forth below in conjunction with the accompanying figures are exemplary descriptions to explain the technical solutions of the embodiments of the present invention and do not constitute a limitation of the technical solutions of the embodiments of the present invention.

It will be understood by technicians in the art unless expressly stated, the singular forms "one," "a", "said," and "the" as used herein" may also include the plural form. It should be understood that when we refer to a component being "connected" or "coupled" to another element, the one component may be directly connected or coupled to the other component, or it may refer to the one component and the other component being connected through an intermediate component. The term "and/or" as used herein refers to at least one of the items defined by the term; for example, "A and/or B" may be implemented as "A or B" or "A and B".

In order to make the purpose, technical solutions and advantages of this application clearer, the following will be described in further detail in conjunction with the accompanying figures for the implementation of this application.

Cardiovascular disease is the leading cause of death and disability worldwide and is the number one killer in the world. Among the multiple causative factors of cardiovascular disease, hypertension ranks first and is the most important risk factor. Once diagnosed, hypertension will require lifelong treatment. Screening for hypertension is usually performed based on clinical blood pressure measurements, but misdiagnosis often occurs due to white coat or occult hypertension. Therefore, outpatient and home blood pressure monitoring has been recommended as the preferred strategy for detecting hypertension and predicting cardiovascular disease risk. A TAG signal is defined as a graphic recording of continuous arterial blood pressure signals that can be acquired by an unobtrusive, wearable, or cuffless continuous arterial blood pressure measurement device. Unlike traditional single and beat-to-beat blood pressure measurements, which can only measure systolic and DBP, the TAG signal consists of a continuous blood pressure waveform and provides a richer set of physiological information, i.e., it not only contains the traditional systolic and DBP, but also reflects other important blood pressure information in addition to these two values, such as tangential marks and other important features or the calculation of cardiac output and peripheral vascular resistance by TAG signals. TAG signals can be used for the evaluation of the cardiovascular system and for the early diagnosis of diseases.

Currently, non-invasive blood pressure monitoring methods such as mercury sphygmomanometer, oscillometric sphygmomanometer, vascular unloading technique aka volumetric clamp method and invasive blood pressure monitoring are commonly used in clinical practice. Methods such as mercury sphygmomanometer and invasive blood pressure monitoring require high operator requirements, invasive blood pressure monitoring has the risk of infection; some equipment is very expensive, such as the volumetric clamp method, these methods are difficult to apply in the home and daily life. Among them, upper arm cuff blood pressure monitors based on oscillometry-based methods are most widely used in out-of-hospital devices. However, upper arm cuffs are not convenient enough for ambulatory blood pressure monitoring. In addition, the size of blood pressure cuffs is strictly defined according to the standard recommendations set by the American Heart Association (AHA), making them difficult to miniaturize, which is detrimental to the wearability and non-intrusive nature of upper-arm blood pressure monitors. With the recognition of the importance of blood pressure and the development of measurement technology, cuffless blood pressure measurement has become a trend in blood pressure monitoring, and the IEEE 1708 standard provides evaluation criteria for wearable cuffless blood pressure measurement devices. The cuffless feature allows it to be applied to various wearable carriers that can measure blood pressure anywhere and anytime, such as watches, glasses, cell phones, clothing, electronic skin or skin-fitting flexible devices In order to achieve upper arm blood pressure that can be measured easily and quickly in daily life and at home, there are two types of more feasible methods available today: 1) wearable cuffless blood pressure monitoring technologies and 2) finding alternative body sites that can reduce the size of the cuff. Currently, cuffless methods must still address the issue of calibration and recalibration before widespread use can be achieved (readings from sample blood pressures measured by cuff-based blood pressure measurement devices are still needed as a reference).

As an alternative solution to upper-arm blood pressure monitoring-based measurements, oscillometric blood pressure monitoring devices with small inflatable cuffs performed at the finger position have been developed and investigated by researchers. It has been shown that, with the use of an appropriately sized cuff and at the same height as the heart, the distal end of the finger, the fingertip, can be a superior alternative location for oscillometric blood pressure measurements that are comparable and essentially identical to upper arm blood pressure values. Not only is the required cuff size minimal, but it also provides the most consistent average blood pressure with the upper arm. In addition, because the finger has easily sensed peripheral arterial vessels, it is also able to collect other precise data about vital body signals, taking the potential use of finger health monitoring even further, such as blood oxygen levels, sleep monitoring, glucose levels, body composition analysis, and hematocrit levels. Compared to smart bracelets worn on the wrist, there is still a little distance from the body, not enough fit, and susceptible to motion noise, making it difficult to detect the actual state of physiological signals accurately.

In recent years, there has also been some research on health monitoring methods and devices worn on the finger, and some companies, such as Ōura, Wellue, K Ring, Helios, ORII, and Go2Sleep have launched some smart ring products. However, most of these ring designs and products are mainly functional in step counting, sleep monitoring, heart rate, blood oxygen level monitoring, and still no continuous blood pressure monitoring and calibration, in addition, some products are still large, which may affect the user's lifestyle demeanor. Some studies and designs, such as the finger ring device with optical sensors to monitor physiological signals (US2021/0169345A1), the dual finger ring design with potential applications for physiological signal monitoring (US 2021/0096657 A1), and the smart ring that can monitor pulse wave signals (CN 106510666 A), although there are innovations in the ring design or sensor arrangement, noise reduction, and acquisition of Although there are innovations in ring design or sensor arrangement, noise reduction, and signal acquisition, there is still no continuous blood pressure acquisition and calibration function; the finger ring type physiological information monitoring device (CN 1692874A), which can acquire beat-to-beat continuous blood pressure information, but no calibration function; some designs such as (U.S. Pat. No. 7,674,231 B2), (U.S. Pat. No. 8,313,439 B2), which can be calibrated but have less description of continuous Some designs such as (U.S. Pat. No. 7,674,231 B2), (U.S. Pat. No. 8,313,439 B2), which can be calibrated but have less description of the continuous blood pressure estimation model; the torso-sensitive network-based finger-applicable cuffless blood pressure monitoring and automatic calibration device (CN 101773387 B), the finger ring device for continuous blood pressure estimation and calibration (U.S. Pat. No. 7,641,614 B2), etc., which not only obtains continuous blood pressure information but also has an automatic calibration function, but some of these blood pressure monitoring functions require additional equipment for However, some of these blood pressure monitoring functions require extra equipment for initial calibration, or the continuous blood pressure estimation simply fits the PPG signal to the blood pressure information by virtue of linearity or nonlinearity, which needs to be improved in accuracy and may require frequent calibration.

The present application provides calibration methods, devices, electronic devices, computer-readable storage media, and computer program products for determining blood pressure estimation models for TAG signals and is intended to solve technical problems of the prior art such as the above.

The technical solutions of the embodiments of the present application and the technical effects produced by the technical solutions of the present application are described below through the description of several exemplary embodiments. It should be noted that the following embodiments can be cross-referenced, borrowed, or combined with each other, and the descriptions of the same terms, similar features, and similar implementation steps, etc. in different embodiments will not be repeated.

FIG. 1 is a schematic diagram of the system architecture provided by an embodiment of the present application for realizing the measurement and display of a TAG signal by a blood pressure estimation model, including a target ring-type device 110, an external display device 120 and a storage platform 130, and the data interaction between the three after establishing a communication connection, wherein the target ring-type device 110 is a device with multiple sensors, and the target ring-type device 110 can collect multiple physiological signals, and the blood pressure information of the target object can be obtained by inputting the collected multiple physiological signals to the target blood pressure estimation model; the external display device 120 can display the multiple physiological signals, blood pressure information, etc. collected by the target finger ring-type device 110; the storage platform 130 can store the multiple physiological signals, blood pressure information, etc. collected by the target finger ring-type device 110, and the storage platform 130 can be a The storage platform 130 may be a cloud database 131 or a telemedicine platform 132, etc., and the present application embodiment does not limit this.

A method of calibrating a blood pressure estimation model for determining TAG signals is provided in embodiments of the present application, as shown in FIG. 2, the method comprising:

Step S201, in response to applying a predetermined degree of first pressure to the first predetermined position, determines the PTT of each pulse wave in the predetermined region at each moment during the predetermined action of the predetermined part of the target object during the plurality of predetermined time periods; the predetermined region is a region with the first predetermined position as the starting position.

The first pre-determined position of the application embodiment refers to the distal end of the finger of the target subject, i.e., the fingertip, which is worn with a target finger ring type device, which is a device with adjustable diameter or contact pressure, made of a material that is not easily deformable, giving a uniform circular constant pressure on the fingertip, i.e., the first pressure.

The target finger ring type device of this application embodiment has a variety of sensors, a variety of sensors can be used to collect a variety of physiological signals, a variety of sensors such as PPG sensors, ECG sensors, pressure sensors, and accelerometers and so on.

Figure 3A:
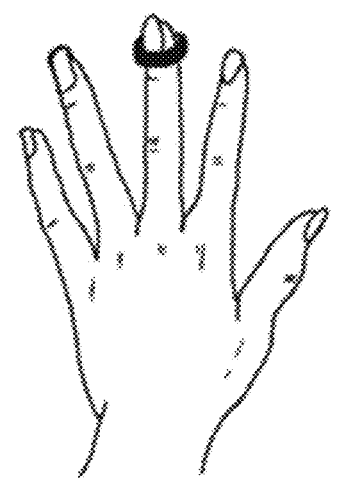
FIG. 3a shows a schematic diagram of the wearing position of a target finger ring type device provided in an embodiment of the present application.
Figure 3B:
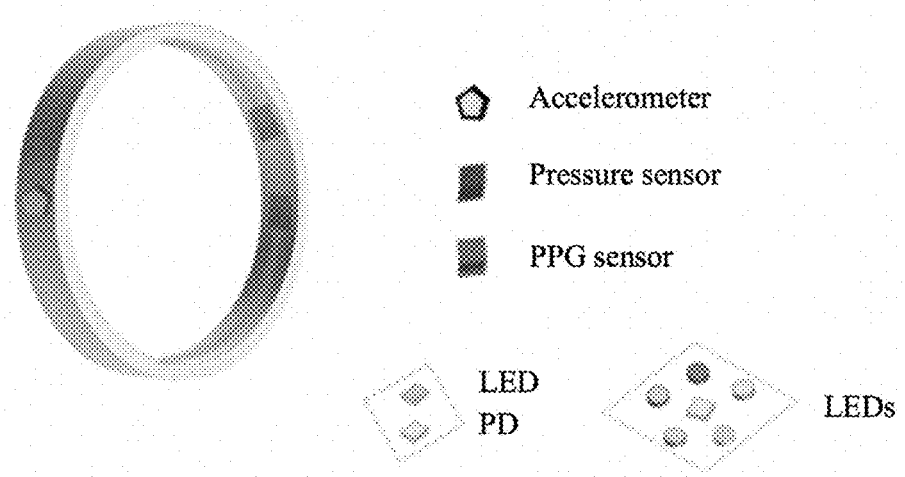
FIG. 3b shows a schematic diagram of the structure of a target finger ring type device provided in an embodiment of the present application.

In this case, the target finger ring type device has a PPG sensor consisting of a red/infrared LED or a multi-wavelength PPG sensors consisting of an LED, a photodetector (PD) and a pressure sensor at the finger ring in contact with the finger belly, and an accelerometer at the finger ring in contact with the nail. The design considers that the finger ventral position is rich in easily sensed peripheral arterial vessels for obtaining a good quality signal, and the accelerometer is located at the nail position is to avoid the influence of the accelerometer by blood pressure pulsation related signals. In this invention, the selection and placement of the sensors is only one embodiment of the invention, as shown in FIG. 3a, which exemplarily illustrates a schematic diagram of the wearing position of the target finger ring type device, located at the fingertip of the target subject; and as shown in FIG. 3b, which exemplarily illustrates a schematic diagram of the structure of the target finger ring type device of this application, which includes an accelerometer, a pressure sensor, a PPG sensor, an LED photodetector, and a plurality of LEDs.

The target finger ring type device of this application embodiment includes, but is not limited to, a buckle strap design, a magnetic suction design, a button design, and a small inflatable cuff design.

Figure 4A:
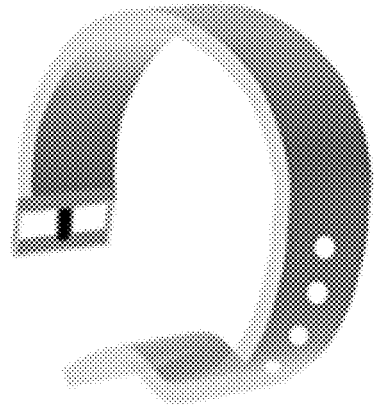
FIG. 4a shows a schematic diagram of a target finger ring device with a buckle strap design
Figure 4B:
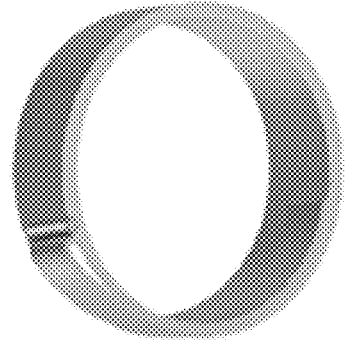
FIG. 4b shows a schematic diagram of a target finger ring device with a magnetic suction design.
Figure 4C:
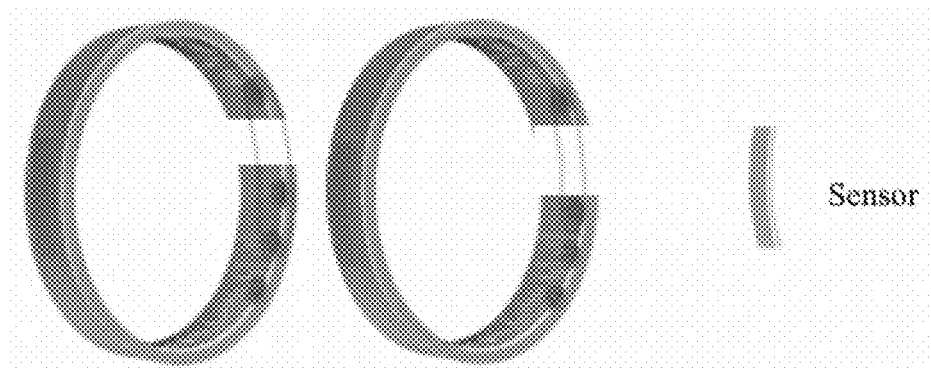
FIG. 4c shows a schematic diagram of a target finger ring device of button design.
Figure 4D:
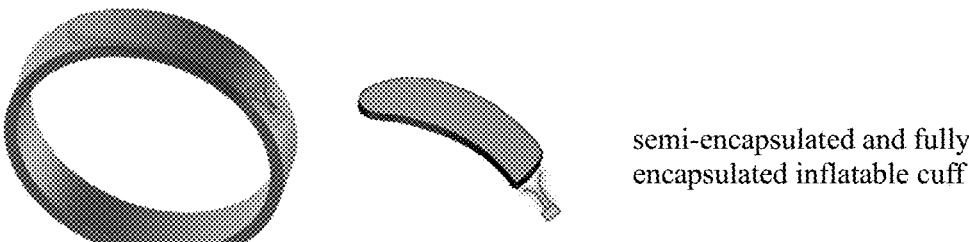
FIG. 4d shows a schematic diagram of a small inflatable cuff design for a target finger ring device.
Figure 6:
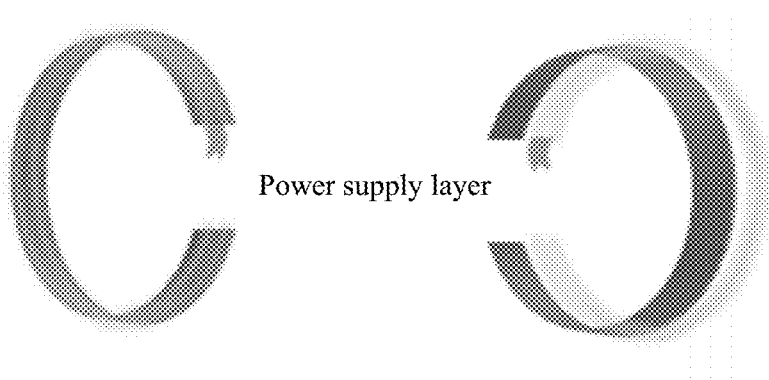
FIG. 6 shows a schematic diagram of the electrical wiring of the adjustable finger ring supply layer.

As shown in FIG. 4a-4d, which exemplarily illustrates several types of target finger ring type devices, 4a shows a snap-band design, 4b shows a magnetic suction design, FIG. 4c shows a button design, and 4d shows a small inflatable cuff design, the small inflatable cuff design includes a semi-encapsulated and fully encapsulated inflatable cuff structure; wrapped around the fingertips during use; a miniature air pump, which inflates the small inflatable cuff Inflation, which pressurizes the measurement site to a pressure exceeding the body's systolic pressure; and a pressure relief valve, which is used to achieve uniform pressure relief of the air in the detachable cuff, after sample blood pressure information based on the oscillometric method is comfortably worn on the proximal end of the finger after pressure relief, and blood pressure information is obtained by calibrating a pre-established initial blood pressure estimation model.

The adjustable target finger ring type device of this application embodiment consists of 4 layers as shown in FIG. 5a; the outermost layer, the third layer, the second layer, and the innermost layer are shown in order in FIGS. 5b-5e. The outermost layer shown in FIG. 5b is composed of hard material that is not easily deformed to protect the internal structure from external damage; the third layer shown in FIG. 5c is the electrical wiring diagram of the power supply layer of the adjustable finger ring, which is used to supply power to the sensors and transmit signals. The second layer shown in FIG. 5d is the sensor distribution layer, with LED, photodiode, accelerometer, pressure sensor and other sensing components; the innermost layer shown in FIG. 5e (near the skin layer), in order to prevent direct contact between the skin and the sensor distribution layer, sweat and other interference with the sensor and the circuit, the use of transparent film silicone and other materials, transparent, smooth, does not interfere with the transmission of optical signals, so that the finger ring shell to maintain a sealed state, waterproof, sweat-proof.

The application embodiment preset part is the arm of the target object, the preset action process is the arm repeated n times stay at different heights or uniform speed for n times arm straightening lifting and lowering process, the application embodiment determines the PTT of the preset region, the preset region is the first preset position as the starting position, that is, the finger tip of the finger as the starting position, the second preset position as the ending position, the second preset position can be the user's wrist or the proximal end of the finger, the preset area is a local area, specifically, the second preset position can be the user's wrist, the target object's wrist has a wearable device, such as a watch, the watch can collect the PPG signal at the wrist, or can be other parts, other parts have wearable external electronic devices that can collect the PPG signal, for example, can collect In particular, the second preset position can be the proximal end of the finger of the user, when the second preset position is the proximal end of the finger, the proximal end of the finger of the target object wears a non-adjustable finger ring, that is, the target object wears a double finger ring, the adjustable target finger ring type device of the fingertip and the non-adjustable finger ring type device of the proximal end of the finger, both of which are made of a material that is not easily deformed. The finger ring worn on the proximal end of the finger is a non-adjustable finger ring type device that captures at least one signal of blood pulsation information and is located on the palm side.

Figure 7A:
FIG. 7a shows a schematic diagram of the design of the target finger ring device in combination with the watch.
Figure 7B:
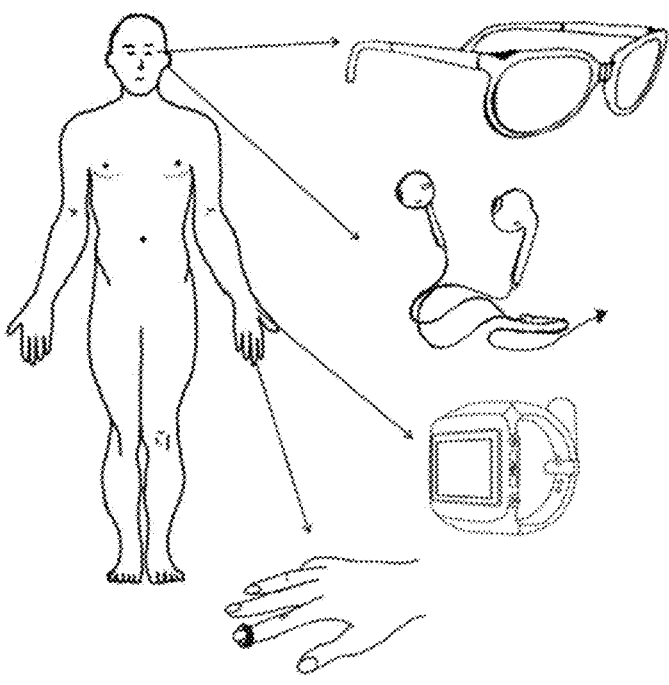
FIG. 7b shows a schematic diagram of the design of the target finger ring device in combination with various other external electronic devices.

As shown in FIGS. 7a-7b, which exemplarily illustrates the schematic diagram of the target ring-type device of the present application embodiment designed in combination with various external electronic devices, FIG. 7a shows a schematic diagram of the combined design of a watch and an adjustable target ring-type device, where the watch is an external electronic device; FIG. 7b shows a schematic diagram of the combined design of the target ring-type device with various other external electronic devices.

Compared with the smart bracelet worn on the wrist, there is still a little distance from the body, the degree of fit is not enough, easy to be affected by the movement noise, it is difficult to accurately detect the real situation of the physiological signal, therefore, this application embodiment prefers a double finger ring design, that is, the distal end of the finger (fingertip) wears an adjustable target finger ring type device, and the proximal end of the finger wears a non-adjustable finger ring type device.

Figure 8A:
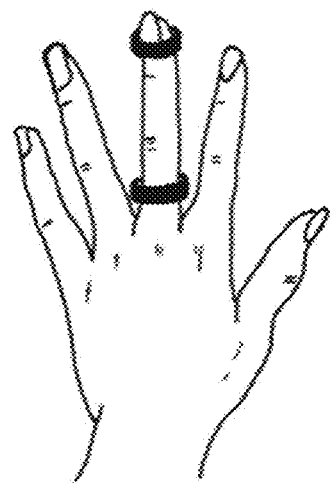
FIG. 8a shows a schematic diagram of the wearing position of the two finger ring devices in the dual finger ring design during the measurement.

As shown in FIG. 8a, an exemplary diagram illustrating the wearing positions of two finger ring-type devices in a dual finger ring design during measurement is shown, where the adjustable target finger ring-type device is located at the distal (fingertip) end of the finger and the non-adjustable finger ring-type device is located at the proximal end of the finger.

Figure 8B:
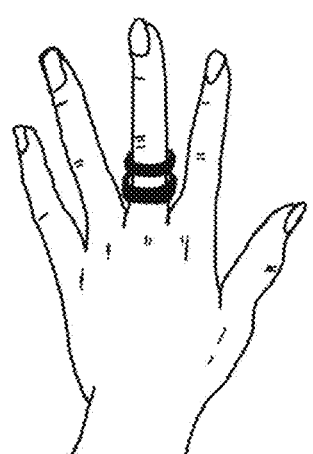
FIG. 8*b* shows a schematic diagram of the wearing position of the two finger ring devices in a non-measurement process in a dual finger ring design.

As shown in FIG. 8b, which exemplarily illustrates the wearing position of two finger ring-type devices in a dual finger ring design during non-measurement, both the adjustable target finger ring-type device and the non-adjustable finger ring-type device are located proximal to the finger, with the proximal end of the finger not interfering with the daily life of the target subject.

With the use of an appropriately sized cuff and at the same height as the heart, the distal end of the finger, the fingertip, can be a superior alternative location for oscillometric blood pressure measurements that are comparable and essentially identical to upper arm blood pressure values. Not only is the required cuff size minimal, but it also provides the most consistent average blood pressure with the upper arm. In addition, because the finger has easily sensed peripheral arterial vessels, it is also able to collect other precise data about important body signals, taking the potential use of finger health monitoring even further, such as blood oxygen levels, sleep monitoring, glucose levels, body composition analysis, and hematocrit levels.

In this application embodiment, after applying a predetermined degree of first pressure to the first predetermined position by the target finger ring type device, the local PTT change is obtained by the finger ring type device in combination with the external electronic device or the dual finger ring device during a predetermined time period when the arm repeats n times to stay at different heights or n times to raise and lower the arm straightening at a uniform speed, and the local PTT change of the predetermined area is obtained by the finger ring type device in combination with the external electronic device or the dual finger ring device, i.e., the PTT of each pulse wave in the predetermined area at each moment is determined.

The local PTT refers to the time difference between the wave crests of two reflective blood pulsation signals, such as two PPG signals, for the same heartbeat cycle. In embodiments of the present application, the two reflective blood pulsation signals may come from the adjustable finger ring device and the proximal finger ring device in a dual finger ring design; or one from the PPG signal of the finger ring type device reflecting the blood pulsation signal and the other reflective blood pulsation signal from an external electronic device such as other wearable blood pressure monitoring devices, such as watches, glasses, and headphones.

Step S202, for performing a derivation for a curve composed of the respective PTT at a respective moment of time within each of the preset time period, determining a moment of time when a derivative satisfies a first preset condition as a first moment of time; acquiring a first pressure of each of the first moment of time, acquiring a second pressure according to a distribution of the first pressure of all the first moment of time; acquiring a first height difference of the first preset location at the first moment of time relative to a heart location; obtaining a first target height difference according to a distribution of all the first height differences;

determining a sample blood pressure information within the preset time period according to the second pressure and the first target height difference; the sample blood pressure information comprises at least one of a sample mean blood pressure, a sample SBP and a sample DBP; the sample blood pressure information includes at least one of the sample average blood pressure, the sample SBP, and the sample DBP.

For each preset time period, the present application embodiment, after determining the PTT at each moment within that preset time period, conducts a derivative of the curve composed of each PTT, and determines the moment when the derivative meets the first preset condition as the first moment, and for the first order derivative dPTT, it can be determined that the moment when the dPTT is maximum within that preset time period is the first moment, and at the first moment, the first preset position. However, as the target's arm is constantly repeated n times staying at different heights or in constant repetitive straightening lifting and lowering, during the repetitive action, the blood pressure hydrostatic pressure (BHP) out of the first preset position is also changing. BHP is also changing, i.e., the blood pressure of the target subject is affected by the blood pressure hydrostatic pressure at this time.

The first pressure is the pressure applied by the target finger ring type device to the first predetermined position, and the pressure signal can be obtained by the pressure sensor in the target finger ring type device to determine the first pressure, and in the predetermined time period, there are multiple first moments, and to reduce the error in measuring the first pressure, the second pressure can be obtained based on the distribution of the first pressure at all first moments, specifically, the mean value of all first pressures $P_{Pi}$ can be determined $P_p$ is the second pressure, and the second pressure is likewise denoted by $P_p$. At zero pressure across the wall, the second pressure is the pressure applied to the fingertip by the target finger ring-type device, which can be viewed as the average blood pressure of the target object $MBP_h$, as the average blood pressure affected by the static blood pressure $MBP_h$, and therefore, the effect of the static blood pressure on the measured average blood pressure needs to be corrected to obtain a more accurate average blood pressure, in order to include this more accurate average blood pressure in the subsequent process as the sample mean blood pressure.

This application embodiment in order to reduce the influence of blood static pressure on the measurement, it is necessary to determine the first height difference $\Delta h_{pi}$ of the first predetermined position relative to the heart position at each first moment, the heart position can be the position of the heart center, and obtain the first target height difference $\Delta h_{pi}$ according to the distribution of all the first height differences; specifically, the average value of all the first height differences $\Delta h_{pi}$ can be used as the first target height difference $\Delta h_{pi}$, and the first target height difference is likewise expressed as $\Delta h_p$.

Embodiments of the present application may detect the change in body position of the target object by means of a gyroscope or an accelerometer, to determine the first height difference of the first predetermined position relative to the heart position during the raising and lowering of the arm as described above.

After determining the second pressure and the first target height difference, the embodiment of this application can correct the blood static pressure in the second pressure according to the first target height difference, and the blood pressure obtained is the average blood pressure of the target object, and the blood pressure information is used as the sample average blood pressure for determining the calibration parameters in the blood pressure model, and the sample average blood pressure is one kind of sample blood pressure information, and the sample blood pressure information measured by the embodiment of this application also includes sample SBP, sample DBP, and sample pulse pressure, and the detailed process of determining the sample SBP, sample DBP, and sample pulse pressure is described in the subsequent section.

The sample blood pressure information of this application embodiment is the blood pressure information required for the calibration phase of the blood pressure estimation model, which can also be referred to as the calibration blood pressure. After determining the sample blood pressure information, this application embodiment can input the sample blood pressure information and the sample physiological signal collected at the first moment into the initial blood pressure estimation model to determine the calibration parameters in the blood pressure estimation model.

In step S203, based on the sample blood pressure information for a plurality of predetermined time periods and the sample physiological signals, the initial blood pressure estimation model, which was established in advance to indicate the relationship between the blood pressure information and the physiological signals, is calibrated to obtain a target blood pressure estimation model.

This application embodiment records various physiological signals of the target object, including but not limited to PPG signals, ECG signals, ultrasound signals and pressure signals, etc., when the arm repeats n times staying at different heights or when the arm performs n times straightening and lowering at a uniform speed, and identifies the physiological signals collected at the first moment as the sample physiological signals.

The blood pressure estimation model of this application embodiment can be any model of measurable blood pressure, inputting sample blood pressure information of a plurality of predetermined time periods and corresponding sample physiological signals into an initial blood pressure estimation model containing at least one calibration parameter, determining the values corresponding to the calibration parameters in the initial blood pressure model, and after determining the values corresponding to each calibration parameter, replacing each calibration parameter with the corresponding value in the initial blood pressure estimation model to obtain a target blood pressure estimation model indicating the relationship between the blood pressure information and the physiological signals.

In the process characterization of the above steps S201-S202 to determine the sample blood pressure information by the PTT of the preset region, if the sample blood pressure information is determined by calculating the PTT from the single wavelength PPG of the preset region acquired by the target finger ring type device in combination with an external device, the PTT and the sample blood pressure information can be expressed by equation (1), which is $$BP = f(PTT) \tag{1}$$

Among them, BP identifies the sample blood pressure information, PTT indicates the single wavelength PTT of the preset region, and equation (1) characterizes the relationship between the sample blood pressure information and the PTT of the preset region, of course, in addition to the form expressed in equation (1), it can also be other forms of equations, in addition to determining the sample PPG through the PTT, other signals can also be introduced for estimation, such as the amplitude of the PPG and other characteristic parameters, which can improve the accuracy of blood pressure estimation to a certain extent.

Step S204, obtains a continuous target physiological signal of the target object, inputs the continuous target physiological signal to the target blood pressure estimation model, and obtains a plurality of beat-to-beat blood pressure information output by the target blood pressure estimation model; the target physiological signal includes a target PPG.

After determining the target blood pressure estimation model, this application embodiment can directly obtain the continuous target physiological signal of the target object, input the continuous target physiological signal to the target blood pressure estimation model, and obtain the plurality of beat-to-beat blood pressure information output by the target blood pressure estimation model.

The target physiological signal is obtained by filtering the original physiological signal collected, and the original physiological signal can be amplified, followed by filtering operation to filter noise interference to obtain the signal band carrying physiological information, and the analog signal is converted to digital signal through the analog-to-digital conversion unit. In the process of signal transmission, since the physiological signal strength is still weak, signal modulation is considered by means of a high frequency and high energy carrier signal to achieve efficient and fidelity transmission over a specific distance.

At the same time, the target PPG acquired by the sensor is combined with the calibrated beat-to-beat blood pressure information, and the cuffless continuous arterial TAG signal and its related information are obtained by transfer function processing.

The blood pressure estimation model established in this application embodiment to obtain continuous beat-to-beat blood pressure information based on multi-wavelength PTT difference (MWPPG TD), etc., can be expressed in Equation (2), which reads $$BP = f(MWPPG\ TD) \qquad (2),$$

where BP identifies the sample blood pressure information and MWPPG TD indicates the multi-wavelength PTT difference, which of course can be other forms than the one expressed in equation (2), and other parameter estimates can be introduced in addition to MWPPG TD.

In step S205, the TAG signal of the target subject is determined from the continuous target PPG as well as the beat-to-beat blood pressure information.

This application embodiment after obtaining the continuous beat-to-beat blood pressure information and the target PPG, determine the pre-established transfer function between the target PPG and the blood pressure information, input the beat-to-beat blood pressure information and the continuous PPG into the transfer function, and obtain the TAG signal output by the transfer function, and the detailed process is described in the subsequent section.

The application embodiment determines the PTT of each pulse wave in a predetermined region at each moment of a predetermined part of the target object during a predetermined action in a plurality of predetermined time periods by applying a predetermined degree of first pressure to a first predetermined position; the predetermined region is a region starting at a first predetermined position; for each predetermined time period, the curve consisting of the PTT at each moment of the predetermined time period is determined as the first moment; for each first moment, the curve consisting of the first pressure at the first moment and the first predetermined position at the first moment is obtained. for each predetermined time period, the derivative of the curve composed of the PTTs for each moment of the predetermined time period is determined, and the moment whose derivative meets the first predetermined condition is the first moment; for each first moment, the first pressure of the first moment and the first height difference of the first predetermined position at the first moment with respect to the heart position are obtained; based on the distribution of the first pressure of all the first moments, the second pressure is obtained; based on the second pressure and the first height difference, the sample blood pressure information of the predetermined time period is determined; the sample blood pressure information of the sample blood pressure information during the predetermined time period; the sample blood pressure information includes at least one of sample mean blood pressure, sample SBP, and sample DBP; based on the sample blood pressure information and sample physiological signals for multiple predetermined time periods, the initial blood pressure estimation model, which was established in advance to indicate the relationship between the blood pressure information and the physiological signals, is calibrated to obtain a target blood pressure estimation model; a continuous target physiological signal of the target subject is obtained, and the continuous target physiological signal of the target subject, inputting the continuous target physiological signal to the target blood pressure estimation model, and obtaining a plurality of beat-to-beat blood pressure information output by the target blood pressure estimation model; the target physiological signal includes a target PPG; and determining a TAG signal of the target subject based on the continuous target PPG and the beat-to-beat blood pressure information. The application embodiment can calibrate the initial blood pressure estimation model by using the sample blood pressure information at the first predetermined location to obtain the target blood pressure estimation model, and the initial blood pressure estimation model can be calibrated without the need for additional sample blood pressure information measured by a cuff blood pressure measurement device.

A possible implementation is provided in an embodiment of the present application to determine the sample blood pressure information for a predetermined time period based on the second pressure as well as the first target height difference, further comprising:

determining that the respective moments in which the oscillation amplitude of the pulse wave determined through the sample PPG at the first predetermined position is a maximum are the second moments;

obtaining the first pressure at each second moment, obtaining a third pressure based on the distribution of the first pressure at all second moments;

obtaining a second height difference relative to the heart position at the first predetermined position at the second moment, obtaining a second target height difference based on the distribution of all the second height differences; and determining the average of the second pressure and the third pressure as the fourth pressure; using the average of the first target height difference and the second target height difference as the third target height difference.

Determining the sample blood pressure information for a predetermined time period based on the fourth pressure as well as the third target height difference.

In addition to determining the sample blood pressure information by the PTT alone, this application embodiment can also measure the sample blood pressure information by combining the PTT with the PPG.

Based on the preceding embodiment, the sample PPG at the first predetermined position is obtained by the target finger ring type device, the oscillatory wave of the pulse wave is determined by this sample PPG, the respective moments when the oscillatory amplitude is a maximum value are determined to be the second moments, and the transmural pressure at the first predetermined position is zero at the respective second moments.

The present application embodiment determines the first pressure of each second moment after determining each second moment, and determines the first pressure $P_{ai}$ of each second moment from the pressure signal collected at each second moment, and takes the average value $P_a$ of the first pressure $P_{ai}$ of each second moment as the third pressure, i.e., the third pressure is expressed as $P_a$.

This application embodiment also needs to determine the second height difference $\Delta h_{ai}$ of the first predetermined position relative to the heart position at each second moment, and the average value $\Delta h_a$ of each second height difference $\Delta h_{ai}$ is used as the second target height difference, i.e., the second target height difference is expressed as $\Delta h_a$.

After determining the first target height difference $\Delta h_p$ as well as the second target height difference $\Delta h_a$, this application embodiment uses the average value of the first target height difference $\Delta h_p$ and the second target height difference $\Delta h_a$ as the third height difference $\Delta h$, i.e $$\Delta h = \frac{\Delta h_a + \Delta h_p}{2}.$$

The embodiment of this application, after determining the second pressure $P_p$ and the third pressure $P_a$, the average value of the second pressure $P_p$ and the third pressure $P_a$ is used as the fourth pressure $$\frac{P_a + P_P}{2},$$

and the fourth pressure is, the fourth pressure is the pressure applied to the fingertip by the target finger ring type device, which can be seen as the average blood pressure $MBP_h$ of the target subject, again the average blood pressure influenced by the static pressure of the blood $MBP_h$, $$MBP_h = \frac{P_a + P_P}{2}.$$

After determining the fourth pressure and the third target height difference, the embodiment of this application can correct the blood static pressure in the fourth pressure according to the third target height difference, and the blood pressure obtained is the average blood pressure of the target object, and the average blood pressure is used as the sample average blood pressure for determining the calibration parameters in the blood pressure model, and the sample average blood pressure is one kind of sample blood pressure information, and the sample blood pressure information measured by the embodiment of this application also includes sample SBP, sample DBP, and sample pulse pressure, and the detailed process of determining the sample SBP, sample DBP, and sample pulse pressure is described in the subsequent section.

A possible implementation is provided in this application embodiment to determine a TAG signal of a target object based on a continuous target PPG as well as beat-to-beat blood pressure information, comprising: determining a pre-established transfer function between the target PPG and the blood pressure information, inputting the beat-to-beat blood pressure information, and the continuous PPG into the transfer function, and obtaining a TAG signal output by the transfer function.

Embodiments of the present application may pre-establish the transfer function between the continuous target PPG and the continuous beat-to-beat blood pressure information, and after obtaining the continuous beat-to-beat blood pressure information as well as the continuous PPG through the blood pressure estimation model, input the beat-to-beat blood pressure information, the continuous PPG into the transfer function, and obtain the TAG signal output by the transfer function.

Figure 9:
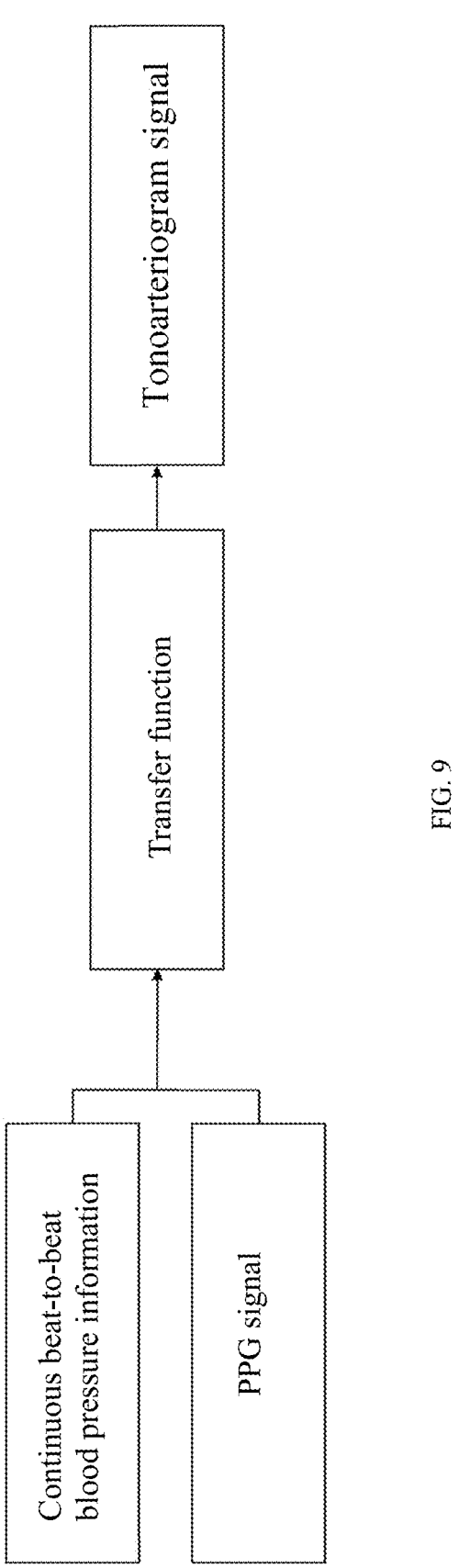
FIG. 9 shows a schematic diagram of obtaining a continuous TAG signal.

As shown in FIG. 9, this application embodiment provides a schematic diagram for obtaining a continuous TAG signal, establishing a transfer function between the continuous beat-to-beat blood pressure information and the PPG, obtaining the blood pressure waveform of the artery by inputting the continuous beat-to-beat blood pressure information and the target PPG, and obtaining the arterial TAG signal by combining it with the beat-to-beat blood pressure information.

A possible implementation is provided in embodiments of the present application to determine sample blood pressure information for each predetermined time period based on the second pressure as well as the first target height difference, comprising:

obtaining a blood density of the target subject, determining a first hemodynamic pressure at a first predetermined location based on the blood density as well as the first target height difference;

determining the sample blood pressure information for each predetermined time period based on the second pressure as well as the first hemodynamic pressure.

The embodiment of this application, after obtaining the first target height difference $\Delta h_p$, yields $BHP_1 = \rho g \Delta h_p$ where $BHP_1$ is the first blood hydrostatic pressure, p is the blood density, and g is the gravitational constant, i.e., the first blood hydrostatic pressure is $\rho g \Delta h_p$.

After using the second pressure as the first average blood pressure affected by the blood pressure static pressure, this application embodiment also determines the diastolic and SBP affected by the blood pressure static pressure, specifically, the blood pressure at a first predetermined percentage of the rising edge of the derivative of the PTT is determined to be the DBP affected by the blood pressure static pressure (the subsequent process is called the first DBP), and the blood pressure at a second predetermined percentage of the falling edge of the derivative of the PTT is determined to be the SBP affected by the blood pressure static pressure (the subsequent process is called the first DBP).

After determining the first average pressure, the first diastolic pressure, and the first systolic pressure affected by the hemodynamic pressure, embodiments of the present application determine the sample average pressure based on the average pressure as well as the first hemodynamic pressure, determine the sample diastolic pressure based on the first diastolic pressure as well as the first hemodynamic pressure, and determine the sample systolic pressure based on the first systolic pressure as well as the first hemodynamic pressure.

A possible implementation is provided in embodiments of the present application to determine the sample blood pressure information for each predetermined time period based on the second pressure as well as the first hemodynamic pressure, comprising:

taking the sum of the second pressure and the first hemodynamic pressure as the sample mean blood pressure;

determining the blood pressure at a first predetermined scale of the rising edge of the derivative as the first systolic pressure, using the sum of the first systolic pressure and the first hemodynamic pressure as the sample systolic pressure; and determining the blood pressure at a second predetermined scale of the falling edge of the derivative as the first diastolic pressure, using the sum of the first diastolic pressure and the first hemodynamic pressure as the sample diastolic pressure.

The embodiment of this application in obtaining the first blood static pressure as $BHP_1=\rho g \Delta h_p$, the sum of the second pressure and the first blood static pressure as the sample mean blood pressure MBP, i.e., $MBP=MBP_h+BHP_1=MBP_h+\rho g \Delta h_p$, where MBP is the sample mean blood pressure, $MBP_h$ is the mean blood pressure affected by the blood static pressure, $BHP_1$ is the first blood static pressure, p is the blood density, and g is the gravitational constant, $\Delta h_p$ is first target height difference.

This application embodiment determines the blood pressure at the first predetermined ratio of the rising edge of dPTT as the first systolic pressure $SBP_h$, the first systolic pressure $SBP_h$ is the blood pressure affected by blood pressure static pressure, and the systolic pressure obtained after correcting for the effect of blood static pressure is the sample systolic pressure SBP, $SBP=SBP_h+BHP_1=SBP_h+\rho g \Delta h_p$, where SBP is the sample systolic pressure, $SBP_h$ is the systolic pressure affected by blood static pressure, BHP 1 is the first blood static pressure, $\rho$ is the blood density, g is the gravitational constant, and $\Delta h_p$ is the first target height difference.

This application embodiment determines the blood pressure at the second predetermined ratio of the falling edge of dPTT as the first diastolic pressure $DBP_h$, the first diastolic pressure DBP h is the blood pressure affected by blood pressure static pressure, and the diastolic pressure obtained after correcting for the effect of blood static pressure is the sample diastolic pressure DBP,$DBP=DBP_h+BHP_1=DBP_h+\rho g \Delta h_p$, where DBP is the sample diastolic pressure, DBP h is the diastolic pressure affected by blood static pressure, $BHP_1$ is the first blood static pressure, p is the blood density, g is the gravitational constant, and $\Delta h_p$ is the first target height difference.

In addition, the sample pulse pressure is the difference between the sample systolic pressure and the sample diastolic pressure.

A possible implementation is provided in this application embodiment to determine the sample blood pressure information for a predetermined time period based on the fourth pressure as well as the third target height difference, comprising:

obtaining a blood density of the target subject, determining a second hemodynamic pressure at a first predetermined location based on the blood density as well as the third target height difference; and determining the sample blood pressure information for the predetermined time period based on the fourth pressure as well as the second hemodynamic pressure.

As in the above embodiment, after determining the third target height difference $$\Delta h = \frac{\Delta h_a + \Delta h_p}{2},$$

the second blood hydrostatic pressure BHP, $$BHP_2 = \rho g \Delta h = \frac{\rho g * (\Delta h_a + \Delta h_p)}{2},$$

is derived based on the third target height difference and the blood density of the target subject.

The embodiment of this application also determines the diastolic and systolic pressures affected by the blood pressure static pressure after using the fourth pressure as the second average blood pressure affected by the blood pressure static pressure.

When the adjustable finger ring is designed as a small inflatable cuff, the fingertip is placed at heart level, and the pressure is uniformly released after the fingertip is pressurized by a miniature air pump to a pressure exceeding the body's systolic pressure, the pressure oscillation wave generated by the pulse beat is obtained through a specific filtering process, the envelope is extracted, and the blood pressure at the third preset ratio along the rising edge of the envelope is determined to be the diastolic pressure influenced by the static blood pressure (the subsequent process is called the second diastolic pressure), and the blood pressure at the fourth preset ratio along the falling edge of the envelope is determined to be the systolic pressure influenced by the static blood pressure (the subsequent process is called the second diastolic pressure).

After determining the second mean pressure, the second diastolic pressure, and the second systolic pressure, embodiments of the present application determine the sample mean pressure based on the second mean pressure as well as the second hemodynamic pressure, determine the sample diastolic pressure based on the second diastolic pressure as well as the second hemodynamic pressure, and determine the sample systolic pressure based on the second systolic pressure as well as the second hemodynamic pressure.

A possible implementation is provided in embodiments of the present application to determine sample blood pressure information for a predetermined time period based on the fourth pressure as well as the second blood pressure static pressure, comprising:

using the sum of the fourth pressure and the second blood pressure static pressure as the sample average blood pressure;

determining an envelope of the oscillatory wave of the sample PPG at a first predetermined position, determining a third predetermined proportional outgoing blood pressure along a rising edge of the envelope as a second systolic pressure, and using the sum of the second systolic pressure and the second blood pressure static pressure as the sample systolic pressure; and determining the blood pressure at the fourth predetermined ratio out of the falling edge of the envelope as the second diastolic pressure and using the sum of the second diastolic pressure and the second blood pressure static pressure as the sample diastolic pressure.

The embodiment of this application in obtaining the second blood static pressure as $$BHP_2 = \frac{\rho g * (\Delta h_a + \Delta h_p)}{2},$$

the sum of the second pressure and the second blood static pressure as the sample mean blood pressure MBP, i.e., $$MBP = MBP_h + BHP_2 = MBP_h + \frac{\rho g * (\Delta h_a + \Delta h_p)}{2},$$

where MBP is the sample mean blood pressure, MBP h is the mean blood pressure affected by the blood static pressure, $BHP_2$ is the second blood static pressure, $\rho$ is the blood density, g is the gravitational constant, his the first target height difference, and $\Delta h_a$ is the second target height difference.

The embodiment of this application determines that the blood pressure at the third predetermined ratio along the rising edge of the envelope is the second SBP$SBP_h$, the second SBP is the blood pressure affected by blood pressure static pressure, and the SBP obtained after correcting for the effect of blood static pressure is the sample SBP SBP, $$SBP = SBP_h + BHP_2 = SBP_h + \frac{\rho g * (\Delta h_a + \Delta h_p)}{2},$$

where SBP is the sample SBP, $SBP_h$ is the SBP affected by blood static pressure, $BHP_2$ is the second blood static pressure, $\rho$ is the blood density, g is the gravitational constant, $\Delta h_p$ is the first target height difference, and $\Delta h_a$ is the second target height difference.

This embodiment of the application determines that the blood pressure at the fourth predetermined ratio along the falling edge of the envelope is the second diastolic pressure $DBP_h$, the second diastolic pressure $DBP_h$ is the blood pressure affected by blood pressure static pressure, and the diastolic pressure obtained after correcting for the effect of blood static pressure is the sample diastolic pressure DBP, $$DBP = DBP_h + BHP_2 == DBP_h + \frac{\rho g * (\Delta h_a + \Delta h_p)}{2},$$

where DBP is the sample diastolic pressure, $DBP_h$ is the diastolic pressure affected by blood static pressure, $BHP_2$ is the second blood static pressure, p is the blood density, g is the gravitational constant, $\Delta h_p$ is the first target height difference, and $\Delta h_a$ is the second target height difference.

A possible implementation is provided in this application embodiment to apply a predetermined degree of first pressure to a first predetermined position, comprising: applying a predetermined degree of first pressure at the first predetermined position by adjusting a diameter or contact pressure of the target finger ring-type device.

The first predetermined position of this application embodiment is the distal end of the finger of the target subject, i.e., the fingertip, and the fingertip is worn with a wearable target finger ring-type device, and a predetermined degree of first pressure can be applied to the first position by adjusting the diameter or contact pressure of the target finger ring-type device.

The application embodiment provides a possible implementation, the target finger ring type device is worn at the first preset position, the first preset position is the distal end of the finger; preset area also includes a second preset position, if the second preset position is the proximal end of the finger, then the second preset position is worn with a non-adjustable, PPG acquisition finger ring type device; if the second preset position is other than the proximal end of the finger, then the second preset position is worn with a corresponding, PPG acquisition external electronic device.

As already described in the previous embodiment, the preset area of this application includes a first preset position and a second preset position, and the PTT at each moment can be determined by the PPG at the first preset position and the second preset position, and the first preset position is worn by a target finger ring type device, which includes a plurality of sensors that can collect a variety of physiological signals; the second preset position also includes a device that can collect the PPG.

If the second predetermined position is the proximal end of the finger, a non-adjustable finger ring type device that collects the PPG is worn at the second predetermined position, and both the first predetermined position and the second predetermined position are finger ring type devices, i.e., the dual finger ring design provided in this application embodiment, and the blood pressure estimation model is calibrated and a continuous TAG signal is obtained by the dual finger ring design.

The second predetermined position can also be other than the proximal end of the finger, the second predetermined position wears a corresponding external electronic device that can collect the PPG, such as a smart watch at the wrist (the wrist is the second predetermined position, the smart watch is an external electronic device), and the eye (the eye is the second predetermined position, the smart glasses is an external electronic device), and the ear (the ear is the second predetermined position, the smart headset is an external electronic device), smart glasses on the eye (eye at the second predetermined position, smart glasses as external electronic device), and smart headphones on the ear (ear at the second predetermined position, smart headphones as external electronic device), i.e., the design provided by the present application embodiment according to the target ring-type device combined with external electronic devices, by which the blood pressure estimation model can also be calibrated and continuous TAG signals can be obtained.

Figure 10:
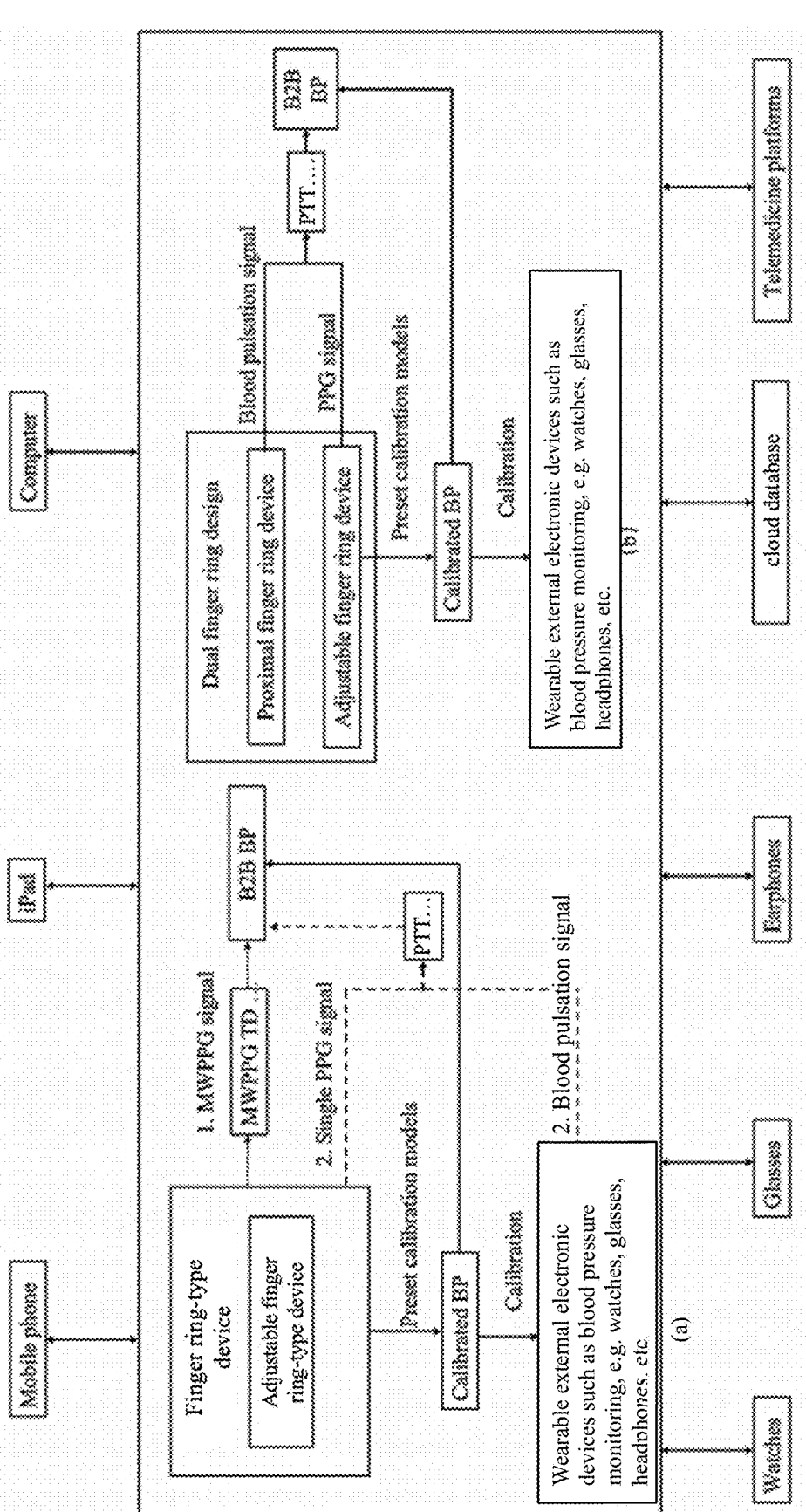
FIG. 10 shows a schematic diagram of the two designs for obtaining calibrated and continuous blood pressure information.

FIG. 10 shows a schematic diagram of obtaining calibrated blood pressure information and continuous blood pressure information under the two designs provided in this application embodiment, as shown in part (a) of FIG. 10. The blood pressure evaluation parameters such as local PTT are calculated from the single PPG obtained by the ring-type device and the information reflecting blood pulsation obtained by the external electronic device, and a continuous blood pressure estimation model is established, and the blood pressure values obtained by the ring-type device are used to calibrate the blood pressure estimation model. If it is a multi-wavelength PPG, blood pressure evaluation parameters such as multi-wavelength PTT difference (MWPPG TD) are obtained, and continuous beat-to-beat blood pressure information is obtained according to its preset multi-wavelength estimation continuous blood pressure model.

In the dual finger ring design, as shown in part (b) of FIG. 10, the target finger ring-type device can be calibrated to other wearable blood pressure monitoring and other external electronic devices through a wireless communication unit;

or the PPG and calibrated blood pressure information acquired by the finger ring-type device can be transmitted to the finger proximal finger ring device at a distance; the blood pressure assessment parameters such as local PTT can be acquired by the dual finger ring device to establish a continuous blood pressure estimation model, and the sample blood pressure information acquired by the adjustable target finger ring-type device can be used for calibration to acquire continuous beat-to-beat (B2B) blood pressure information without a cuff.

One possible implementation is provided in this application embodiment, where the sample PPG or the target PPG is filtered in the following manner, acquiring the original PPG of multiple channels.

For the original PPG of any one channel, the target component in the PPG is extracted by integrating the constrained independent component analysis, adaptive filtering, and no underlying source quantity assumption method, and the target component is input to the adaptive filter to instruct the adaptive filter to recover the PPG according to the target component to obtain the sample PPG or the target PPG.

In the preceding embodiment, the application embodiment obtains a sample PPG to refine the estimation model, and after the blood pressure estimation model is built, continuous beat-to-beat blood pressure information is obtained by inputting the continuous target PPG into the blood pressure estimation model.

The filtering method of the sample PPG or the target PPG involved above applies a method that integrates constrained independent component analysis (cICA) and adaptive filters in the time domain to reduce the motion artifact (MA) problem for multiple photoelectric signals.

Specifically, firstly, the constrained independent component analysis is used to extract the PPG target component based on the periodic information of the PPG, but it leads to the missing amplitude information indeed. Subsequently, the adaptive filtering algorithm is invoked to recover this amplitude information, where the PPG target component is used as the reference input of the adaptive filter.

Unlike traditional independent component analysis algorithms, constrained independent component analysis does not make assumptions about the actual number of underlying sources. The algorithm does not need to assume the actual number of underlying sources and can automatically extract specific sources, which means that the problem of MA signals being a complex combination of multiple sources can be solved. Therefore, the components of interest are automatically obtained using constrained independent component analysis. In addition, the adaptive filter is used to effectively reduce the MA by recovering the amplitude information of the PPG.

Figure 11:
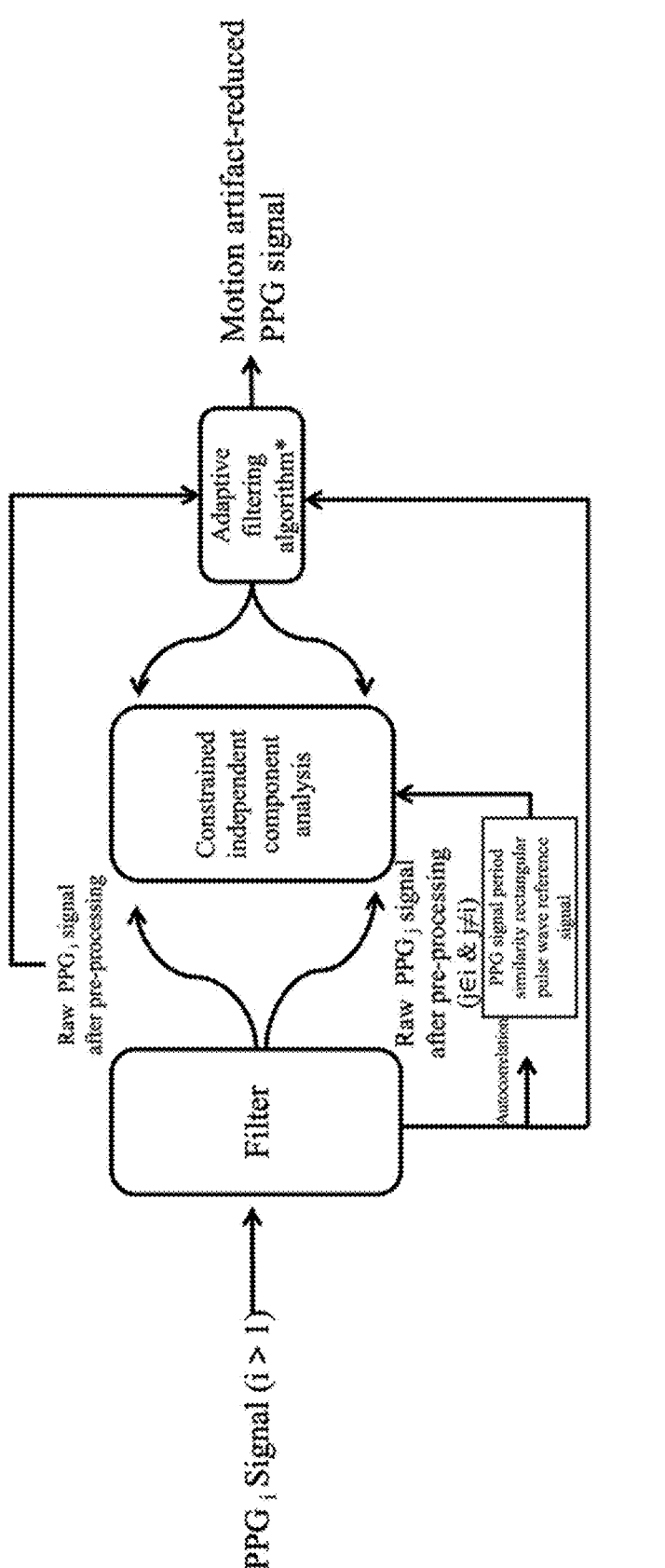
FIG. 11 shows a schematic diagram of noise reduction by means of constrained independent component analysis and adaptive filtering.

As shown in FIG. 11, which exemplarily illustrates the noise reduction by means of constrained independent component analysis (cICA) and adaptive filtering: (a) The original PPG of multiple channels are first processed by a filter to remove high frequency noise and DC components. (b) Any channel signal is selected for autocorrelation and other processing to obtain the period of the PPG, and the reference signal for constrained independent component analysis is generated based on the obtained period. (c) Both the multi-channel pre-processed PPG and the reference signal generated in step (b) are fed into the constrained independent component analysis algorithm, which then generates the correlation components of the PPG without artifacts. (d) The correlation component of the PPG without artificial traces is fed into the adaptive filter as the reference input to recover the amplitude information of the PPG of multiple channels, and the damaged PPG of multiple channels is used as the corresponding desired signal respectively to obtain the motion artifact-reduced PPG of multiple channels. In addition, the adaptive filtering algorithm, the number is determined by the number of channels of the PPG, a minimum of two groups.

A possible implementation is provided in this application embodiment, after determining a TAG signal of the target object based on the continuous target PPG and the beat-to-beat blood pressure information, further comprising: sending the TAG signal to an external display device to instruct the external display device to display the TAG signal.

After obtaining the TAG signal, the application embodiment sends the TAG signal to an external display device, which may be an external electronic device other than the target ring-type device at the target, which may interact with the external display device, which includes, but is not limited to, a cuffless wearable blood pressure monitoring device, a cell phone, a tablet, a computer, and other external electronic devices, and may also be uploaded to a cloud database and a remote medical platform to continuously record blood pressure information and analyze it for remote consultation and diagnosis.

The application embodiment also performs an alarm call when abnormal blood pressure information is determined and can send an alarm message to a local ambulance center or an emergency contact to perform an alarm call.

Figure 12:
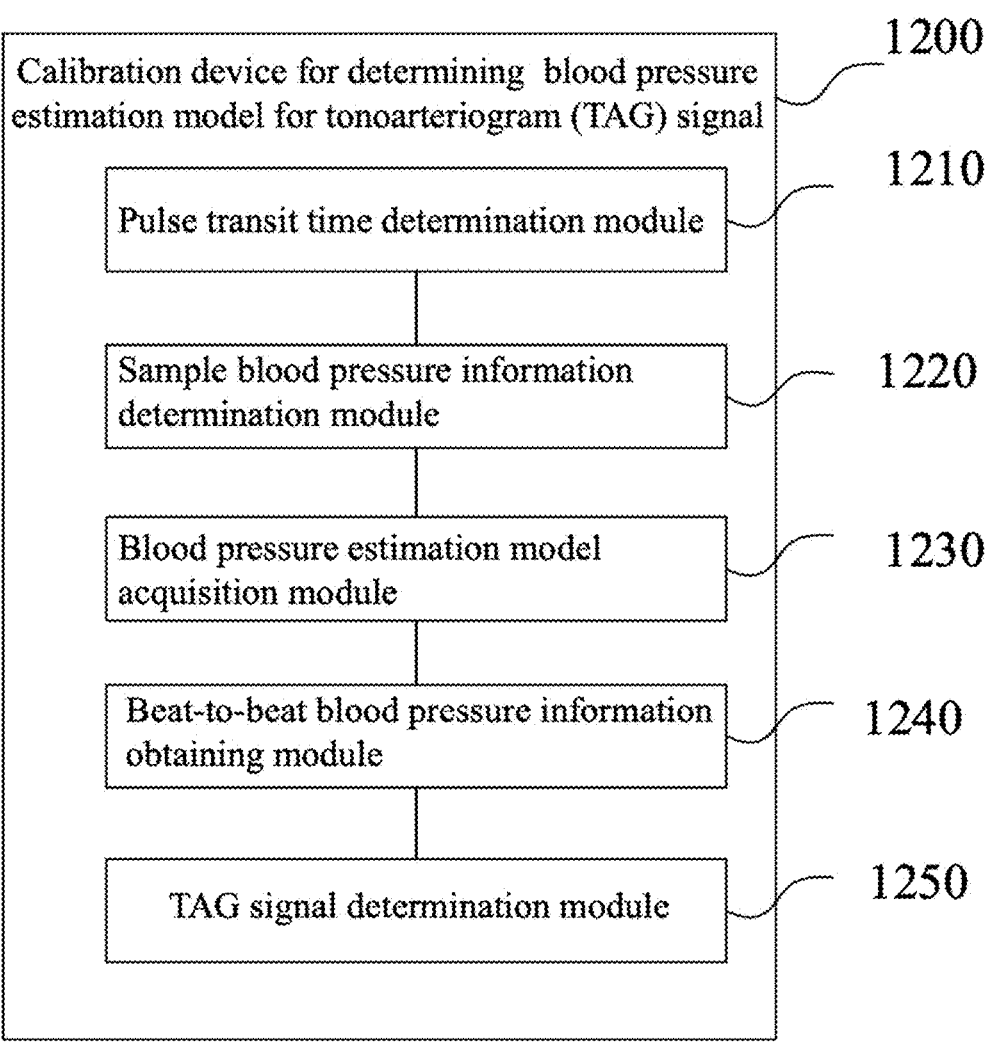
FIG. 12 shows a schematic diagram of the structure of a calibration device for determining a blood pressure estimation model for TAG signals.

Embodiments of the present application provide a calibration device for determining a blood pressure estimation model for a TAG signal, as shown in FIG. 12, wherein the device 1200 may include a PTT determination module 1210 for determining, in response to applying a predetermined degree of first pressure to a first predetermined position, the PTT of each pulse wave in a predetermined region at each moment during a predetermined action at a predetermined part of the target object during a plurality of predetermined time periods; the predetermined region being a region with the first predetermined position as the starting position;

sample blood pressure information determination module 1220 for, for each predetermined time period, deriving the curve consisting of the conduction time of each pulse wave at each moment in the predetermined time period, determining the moment at which the derivative meets the first predetermined condition as the first moment; obtaining the first pressure at each first moment, obtaining the second pressure based on the distribution of the first pressure at all first moments; obtaining the first height difference of the first predetermined position at the first height difference relative to the heart position at the first moment, and obtaining the first target height difference based on the distribution of all the first height differences; determining the sample blood pressure information for the predetermined time period based on the second pressure and the first target height difference; the sample blood pressure information includes at least one of the sample average blood pressure, the sample SBP, and the sample DBP;

a blood pressure estimation model acquisition module 1230 for obtaining a target blood pressure estimation model based on sample blood pressure information for a plurality of predetermined time periods and sample physiological signals, calibrating an initial blood pressure estimation model built in advance indicating a relationship between the blood pressure information and the physiological signals; and a beat-to-beat blood pressure information obtaining module 1240 for obtaining, at a first predetermined position of a target object, consecutive target physiological signals, inputting the consecutive target physiological signals to the pre-constructed target blood pressure estimation model, and obtaining a plurality of beat-to-beat blood pressure information output by the target blood pressure estimation model; the target physiological signals include a target PPG signal.

A TAG signal determination module 1250 for determining a TAG signal of the target object based on the continuous target PPG signals and the beat-to-beat blood pressure information.

The application embodiment determines the PTT of each pulse wave in a predetermined region at each moment of a predetermined part of the target object during a predetermined action in a plurality of predetermined time periods by applying a predetermined degree of first pressure to a first predetermined position; the predetermined region is a region starting from a first predetermined position; for each predetermined time period, the curve consisting of the PTT at each moment of the predetermined time period is determined as the first moment; for each first moment, the curve consisting of the first pressure at the first moment and the first predetermined position at the first moment is obtained. For each predetermined time period, the derivative of the curve composed of the PTTs for each moment of the predetermined time period is determined, and the moment whose derivative meets the first predetermined condition is the first moment; for each first moment, the first pressure of the first moment and the first height difference of the first predetermined position at the first moment with respect to the heart position are obtained; based on the distribution of the first pressure of all the first moments, the second pressure is obtained; based on the second pressure and the first height difference, the sample blood pressure information of the predetermined time period is determined; the sample blood pressure information of the sample blood pressure information during the predetermined time period; the sample blood pressure information includes at least one of sample mean blood pressure, sample SBP, and sample DBP; based on the sample blood pressure information and sample physiological signals for multiple predetermined time periods, the initial blood pressure estimation model, which was established in advance to indicate the relationship between the blood pressure information and the physiological signals, is calibrated to obtain a target blood pressure estimation model; a continuous target physiological signal of the target object, inputting the continuous target physiological signal to the target blood pressure estimation model, and obtaining a plurality of beat-to-beat blood pressure information output by the target blood pressure estimation model; the target physiological signal includes a target PPG signal; and determining a TAG signal of the target object based on the continuous target PPG signal and the beat-to-beat blood pressure information. The application embodiment can calibrate the initial blood pressure estimation model by using the sample blood pressure information at the first predetermined position to obtain the target blood pressure estimation model, and the initial blood pressure estimation model can be calibrated without the need for additional sample blood pressure information measured by a cuff blood pressure measurement device. TAG signal from the target blood pressure model.

A possible implementation is provided in this application embodiment, the sample blood pressure information determination module is also used to determine the respective moments when the oscillation amplitude of the pulse wave determined through the sample PPG signal at the first predetermined position is a maximum value as the second moment; to obtain the first pressure at each second moment, to obtain the third pressure based on the distribution of the first pressure at all second moments; to obtain the second pressure at the first predetermined position at each second moment relative to the heart position, and obtain the second target height difference according to the distribution of all second height differences; determine the average value of the second pressure and the third pressure as the fourth pressure; use the average value of the first target height difference and the second target height difference as the third target height difference; determine the sample blood pressure information during the predetermined time period according to the fourth pressure and the third target height difference.

A possible implementation is provided in this application embodiment, the TAG signal acquisition module comprising: a TAG signal obtaining sub-module for determining a pre-established transfer function between a target PPG signal and blood pressure information, inputting beat-to-beat blood pressure information, a continuous PPG signal into the transfer function, and obtaining a TAG signal output by the transfer function.

A possible implementation is provided in this application embodiment, wherein the sample blood pressure information determination module comprises:

a first hemodynamic pressure determination sub-module for obtaining the blood density of the target object, determining a first hemodynamic pressure at a first predetermined position based on the blood density and the first target height difference; and a sample blood pressure information determination sub-module for determining the sample blood pressure information for each predetermined time period based on the second pressure as well as the first blood static pressure.

A possible implementation is provided in this application embodiment, the sample blood pressure information determination module further comprising:

a sample average blood pressure determination sub-module for taking the sum of the second pressure and the first hemodynamic pressure as the sample average blood pressure;

a sample SBP determination sub-module for the blood pressure at a first predetermined ratio of the rising edge of the derivative as the first SBP, using the sum of the first systolic pressure and the first hemodynamic pressure as the sample SBP; and a sample diastolic pressure determination sub-module for the blood pressure at a second predetermined ratio of the falling edge of the derivative as the first diastolic pressure, taking the sum of the first diastolic pressure and the first hemodynamic pressure as the sample diastolic pressure.

A possible implementation is provided in this application embodiment, the sample blood pressure information determination module further comprising:

a second hemodynamic pressure determination submodule for obtaining a blood density of the target subject, determining a second hemodynamic pressure at the first predetermined location based on the blood density and the third target height difference; and a sample blood pressure information determination submodule for determining sample blood pressure information for a predetermined time period based on the fourth pressure as well as the second blood static pressure.

A possible implementation is provided in this application embodiment, the sample blood pressure information determination module further comprising:

a sample average blood pressure determination sub-module for using the sum of the fourth pressure and the second blood pressure static pressure as the sample average blood pressure;

a sample SBP determination submodule for determining the envelope of the oscillatory wave of the sample PPG signal at the first predetermined position, determining the third predetermined proportional outgoing blood pressure at the rising edge of the envelope as the second SBP, and using the sum of the second systolic pressure and the second blood pressure static pressure as the sample SBP; and a sample diastolic pressure determination submodule for determining that the blood pressure at a fourth predetermined ratio out of the falling edge of the envelope is a second diastolic pressure and using the sum of the second diastolic pressure and the second blood pressure static pressure as the sample diastolic pressure.

A possible implementation is provided in this application embodiment, wherein the PTT determination module comprises: a first pressure application sub-module for applying a pre-determined degree of first pressure at a first predetermined position by adjusting a diameter or contact pressure of the target finger ring-type device.

A possible implementation is provided in this application embodiment, where the target finger ring type device is worn at the first predetermined position, the first predetermined position being the distal end of the finger; the predetermined region also includes a second predetermined position, and if the second predetermined position is the proximal end of the finger, then a non-adjustable finger ring type device that collects an optical volume signal is worn at the second predetermined position; if the second predetermined position is other than the proximal end of the finger, then If the second predetermined position is other than the proximal end of the finger, the second predetermined position is worn with a corresponding external electronic device that can collect the PPG signal.

A possible implementation is provided in this application embodiment, where the sample PPG signal or the target PPG signal is filtered as follows: acquiring the original PPG signals of multiple channels.

For the original PPG signal of any one channel, the target component in the PPG signal is extracted by integrating the constrained independent component analysis, adaptive filtering, and no underlying source quantity assumption method, and the target component is input to the adaptive filter to instruct the adaptive filter to reply to the PPG signal according to the target component to obtain the sample PPG signal or the target PPG signal.

A possible implementation is provided in this application embodiment, the device further comprising: a display module for sending a blood pressure graph to an external display device to instruct the external display device to display the blood pressure graph.

The device of the present application embodiment can perform the method provided in the present application embodiment with similar implementation principles. The actions performed by the modules in the device of the present application embodiment correspond to the steps in the method of the present application embodiment, and a detailed functional description of the modules of the device can be specifically found in the corresponding method shown in the previous section, which will not be repeated here.

Provided in this application embodiment is an electronic device comprising a memory, a processor and a computer program stored on the memory, the processor executing the steps of the above-mentioned computer program to implement the calibration method of the blood pressure estimation model, which can be achieved in comparison with related technology: this application embodiment determines, in response to applying a first pressure of a predetermined degree to a first predetermined position, the target object during a plurality of predetermined time periods of preset parts during the preset action, the PTT of each pulse wave at each moment in the preset region; the preset region is a region with the first preset position as the starting position; for each preset time period, the curve consisting of the PTT of each pulse wave at each moment in the preset time period is derived, and the moment at which the derivative meets the first preset condition is determined as the first moment; for each first moment, the first pressure at the first moment and a first height difference between the first predetermined position at the first moment relative to the heart position; obtaining a second pressure based on the distribution of the first pressure at all first moments; determining sample blood pressure information for the predetermined time period based on the second pressure and the first height difference; the sample blood pressure information includes at least one of a sample average blood pressure, a sample SBP, and a sample DBP; based on the sample blood pressure information and sample physiological signals for a plurality of predetermined time periods, calibrating an initial blood pressure estimation model established in advance indicating a relationship between blood pressure information and physiological signals to obtain a target blood pressure estimation model; obtaining a continuous target physiological signal of a target object, inputting the continuous target physiological signal to the target blood pressure estimation model, and obtaining a plurality of beat-to-beat blood pressure outputs of the target blood pressure estimation model. The target physiological signal includes a target PPG signal; the TAG signal of the target object is determined based on the continuous target PPG signal and the beat-to-beat blood pressure information. The application embodiment can calibrate the initial blood pressure estimation model by using the sample blood pressure information at the first predetermined position to obtain the target blood pressure estimation model, and the initial blood pressure estimation model can be calibrated without the need for additional sample blood pressure information measured by a cuff blood pressure measurement device. TAG signal from the target blood pressure model.

Figure 13:
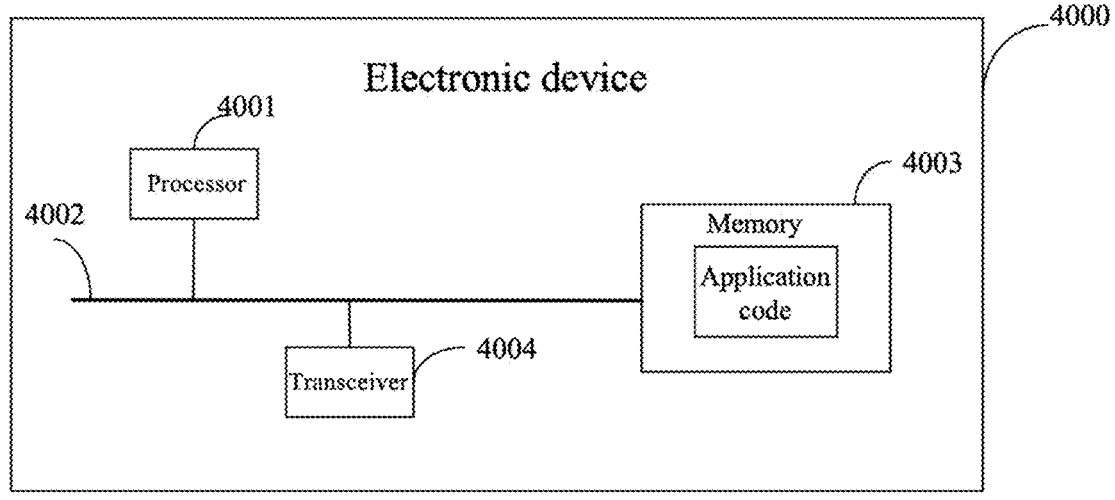
FIG. 13 shows a schematic diagram of the structure of an electronic apparatus.

In an optional embodiment an electronic device is provided, as shown in FIG. 13, wherein the electronic device 4000 shown in FIG. 13 includes: a processor 4001 and a memory 4003. wherein the processor 4001 and the memory 4003 are connected, e.g., via a bus 4002. Preferably, the electronic device 4000 may also include a transceiver 4004, which may be used for data interaction between this electronic device and other electronic devices, such as the sending of data and/or the receiving of data, etc. It should be noted that the transceiver 4004 is not limited to one in practical applications, and the structure of the electronic device 4000 does not constitute a limitation of this application embodiment.

Processor 4001 can be a CPU (Central Processing Unit), a general-purpose processor, a DSP (Digital Signal Processor), an ASIC (Application Specific Integrated Circuit), an FPGA (Field Programmable Gate Array), or any combination thereof. Integrated Circuit), FPGA (Field Programmable Gate Array) or other programmable logic device, transistorized logic device, hardware component, or any combination thereof. It may implement or execute various exemplary logic boxes, modules, and circuits described in conjunction with the disclosure of this application. Processor 4001 may also be a combination that implements a computing function, such as a combination containing one or more microprocessors, a combination of a DSP and a microprocessor, etc.

The bus 4002 may include a pathway to transfer information between the above components. Bus 4002 may be a PCI (Peripheral Component Interconnect) bus or an EISA (Extended Industry Standard Architecture) bus, etc. Bus 4002 can be divided into address bus, data bus, control bus, etc. For the convenience of representation, only one thick line is used in FIG. 13, but it does not mean that there is only one bus or one type of bus.

Memory 4003 may be ROM (Read Only Memory) or other types of static storage devices that can store static information and instructions, RAM (Random Access Memory) or other types of dynamic storage devices that can store information and instructions, or EEPROM (Electrically Erasable Programmable Read Only Memory). EEPROM (Electrically Erasable Programmable Read Only Memory), CD-ROM (Compact Disc Read Only Memory) or other optical disc storage, optical disc storage (including compressed disc, laser disc, optical disc, digital universal CD-ROM (Compact Disc Read Only Memory), CD-ROM (Compact Disc Read Only Memory) or other optical disc storage, optical disc storage (including compressed disc, laser disc, optical disc, digital universal disc, Blu-ray disc, etc.), disk storage media, other magnetic storage devices, or any other media that can be used to carry or store computer programs and can be read by a computer without limitation here.

Memory 4003 is used to store a computer program for executing an embodiment of the present application and is controlled for execution by processor 4001. The processor 4001 is used to execute the computer program stored in the memory 4003 to implement the steps shown in the preceding method embodiment.

Among others, the electronic device package may include, but is not limited to, mobile terminals such as cell phones, laptop computers, digital broadcast receivers, PDAs (personal digital assistants), PADs (tablet computers), PMPs (portable multimedia players), vehicle terminals (e.g., vehicle navigation terminals), and the like, and fixed terminals such as digital TVs, desktop computers, and the like. The electronic device shown in FIG. 13 is only an example and should not impose any limitations on the functionality and scope of use of embodiments of the present disclosure.

Embodiments of the present application provide a computer readable storage medium on which a computer program is stored, the computer program being executable by a processor to implement the steps and corresponding contents of the foregoing method embodiments. Compared with the prior art it can be achieved that: the present application embodiment determines the PTT of each pulse wave at each moment in a predetermined region during a predetermined action of a predetermined part of a target object in a plurality of predetermined time periods by responding to applying a predetermined degree of first pressure to a first predetermined position; the predetermined region is a region with the first predetermined position as a starting position; for each predetermined time period, the PTT of each pulse wave at each moment in a predetermined for each preset time period, the curve composed of the PTTs at each moment of the preset time period is derived, and the moment whose derivative meets the first preset condition is determined as the first moment; for each first moment, the first pressure at the first moment and the first height difference of the first preset position at the first moment with respect to the heart position are obtained; the second pressure is obtained based on the distribution of the first pressure at all first moments; based on the second pressure and the first height difference; determining sample blood pressure information for a predetermined time period; the sample blood pressure information includes at least one of sample mean blood pressure, sample SBP, and sample DBP; obtaining a target blood pressure estimation model based on the sample blood pressure information for a plurality of predetermined time periods and the sample physiological signal by calibrating an initial blood pressure estimation model established in advance indicating a relationship between the blood pressure information and the physiological signal; and Obtaining a continuous target physiological signal of the target subject, inputting the continuous target physiological signal to the target blood pressure estimation model, and obtaining a plurality of beat-to-beat blood pressure information output by the target blood pressure estimation model; the target physiological signal includes a target PPG signal; and determining a TAG signal of the target subject based on the continuous target PPG signal and the beat-to-beat blood pressure information. The application embodiment can calibrate the initial blood pressure estimation model by using the sample blood pressure information at the first predetermined position to obtain the target blood pressure estimation model, and the initial blood pressure estimation model can be calibrated without additional sample blood pressure information measured by a cuff-type blood pressure measurement device, and the entire calibration process is automatic and simple, and the target blood pressure model can be used to obtain a high-precision arterial TAG signal from the target blood pressure model.

It is to be noted that the computer-readable medium described above in this disclosure may be a computer-readable signal medium or a computer-readable medium or any combination of the above. A computer readable storage medium may be, for example—but not limited to—an electrical, magnetic, optical, electromagnetic, infrared, or semiconductor system, device, or device, or any combination of the above. More specific examples of computer-readable storage media may include but are not limited to: electrically connected with one or more wires, portable computer disks, hard disks, random access memory (RAM), read-only memory (ROM), erasable programmable read-only memory (EPROM or flash memory), optical fiber, portable compact disk read-only memory (CD-ROM), optical storage devices, or any of the above. Magnetic memory devices or any suitable combination of the preceding. n the present disclosure, a computer-readable storage medium may be any tangible medium that contains or stores a program that may be used by or in combination with an instruction execution system, device, or device. And in the present disclosure, a computer-readable signal medium may include a data signal propagated in the baseband or as part of a carrier wave that carries computer-readable program code. Such propagated data signals may take a variety of forms, including but not limited to electromagnetic signals, optical signals, or any suitable combination of the foregoing. Computer-readable signal medium can also be any computer-readable medium other than computer-readable storage media, the computer-readable signal medium can send, propagate, or transmit the program for use by or in combination with the instruction execution system, device or device. The program code contained on the computer-readable medium may be transmitted using any suitable medium, including but not limited to wire, fiber optic cable, RF (radio frequency), etc., or any suitable combination of the above.

The present application embodiment also provides a computer program product comprising a computer program, the computer program being executable by a processor to implement the steps and corresponding contents of the foregoing method embodiment. Compared with the prior art it is possible to achieve: the present application embodiment determines the PTT of each pulse wave in a predetermined region at each moment during a predetermined action of a predetermined part of the target object in a plurality of predetermined time periods by responding to applying a predetermined degree of first pressure to a first predetermined position; the predetermined region is a region starting at the first predetermined position; for each predetermined time period, the PTT of each pulse wave at each moment during the predetermined action of the predetermined for each preset time period, the curve composed of the PTTs at each moment of the preset time period is derived, and the moment whose derivative meets the first preset condition is determined as the first moment; for each first moment, the first pressure at the first moment and the first height difference of the first preset position at the first moment with respect to the heart position are obtained; the second pressure is obtained based on the distribution of the first pressure at all first moments; based on the second pressure and the first height difference; determining sample blood pressure information for a predetermined time period; the sample blood pressure information includes at least one of sample mean blood pressure, sample SBP, and sample DBP; obtaining a target blood pressure estimation model based on the sample blood pressure information for a plurality of predetermined time periods and the sample physiological signal by calibrating an initial blood pressure estimation model established in advance indicating a relationship between the blood pressure information and the physiological signal; and Obtaining a continuous target physiological signal of the target subject, inputting the continuous target physiological signal to the target blood pressure estimation model, and obtaining a plurality of beat-to-beat blood pressure information output by the target blood pressure estimation model; the target physiological signal includes a target PPG signal; and determining a TAG signal of the target subject based on the continuous target PPG signal and the beat-to-beat blood pressure information. The application embodiment can calibrate the initial blood pressure estimation model by using the sample blood pressure information at the first predetermined position to obtain the target blood pressure estimation model, and the initial blood pressure estimation model can be calibrated without the need for additional sample blood pressure information measured by a cuff blood pressure measurement device. TAG signal from the target blood pressure model.

The terms "first", "second", "third", "fourth", "1", "2", etc. (if present) in the specification and claims of this application and the accompanying drawings above are used to distinguish similar objects and need not be used to describe a particular order or sequence. It should be understood that the data so used may be interchanged where appropriate so that embodiments of the present application described herein can be implemented in an order other than that illustrated or described in the text.

It should be understood that although the flowcharts of embodiments of the present application indicate the individual operational steps by arrows, the order in which these steps are performed is not limited to the order indicated by the arrows. Unless explicitly stated herein, in some implementation scenarios of embodiments of the present application, the implementation steps in the respective flowcharts may be performed in other orders as desired. In addition, some or all of the steps in each flowchart may include multiple sub-steps or multiple stages based on actual implementation scenarios. Some or all of these sub-steps or phases may be executed at the same moment, and each of these sub-steps or phases may also be executed separately at different moments. In the scenario where the execution time is different, the execution order of these sub-steps or stages can be flexibly configured according to the demand, and this application embodiment is not limited to this.

It should be noted that for a person of ordinary skill in the art, other similar means of implementation based on the technical idea of the present application, without departing from the technical idea of the present application, also fall within the scope of protection of the embodiments of the present application.

The invention claimed is:

1. A method of calibrating a blood pressure estimation model for determining tonoarteriogram (TAG) signals, comprising:

via a device adapted to apply adjustable pressure, applying a pressure to a first location of a body of a target subject; wherein the device adapted to apply adjustable pressure comprises a ring-shaped device, via a PTT determining module:

in response to the pressure applied, detecting a plurality of pulse waves at a region of the body within a preset time period, and determining a plurality of respective pulse transit times (PTT) of said plurality of respective pulse waves at respective moments of time during a movement of the body;

wherein the first location is used as an initial location;

via a sample blood pressure information determining module:

performing a derivation for a curve composed of the plurality of respective PTT at the respective moments of time, and determining a plurality of moments of time when a derivative satisfies a first condition as a plurality of first moments of time;

acquiring a first pressure of each of the first moment of time from the plurality of moments of time;

acquiring a second pressure according to a distribution of the plurality of first pressures of the plurality of first moments of time;

acquiring a first height difference of the first location relative to a heart location at each of the first moment of time;

obtaining a first target height difference according to a distribution of all of the first height differences;

determining a sample blood pressure information within the preset time period according to the second pressure and the first target height difference; the sample blood pressure information comprises at least one of a sample mean blood pressure, a sample systolic blood pressure (SBP) and a sample diastolic blood pressure (DBP);

via a blood pressure estimation model:

based on the sample blood pressure information and a sample physiological signal at a plurality of preset time periods, performing calibration for a pre-established initial blood pressure estimation model indicating a relationship between blood pressure information and physiological signal, and obtaining a target blood pressure estimation model;

via a beat-to-beat pressure information determining module:

acquiring a continuous target physiological signal of the target subject, inputting the continuous target physiological signal to the target blood pressure estimation model; wherein the continuous target physiological signal comprises a continuous target PPG signal;

acquiring a plurality of beat-to-beat blood pressure information output by the target blood pressure estimation model; and via a TAG signals determining module:

determining a TAG signal of the target subject according to the continuous target PPG signal and the plurality of beat-to-beat blood pressure information.

2. The method according to claim 1, wherein the step of determining the sample blood pressure information within the preset time period according to the second pressure and the first target height difference, further comprises:

determining the respective moment of time when an oscillation amplitude of a pulse wave is at a maximum value as a second moment of time, wherein the second moment of time is determined via a sample PPG signal at the first location;

acquiring the first pressure at the respective second moment of time, acquiring a third pressure according to a distribution of the first pressure at all of the second moments of time;

acquiring a second height difference of the first location at the respective second moment of time relative to the heart location, obtaining a second target height difference according to a distribution of all the second height differences;

determining a fourth pressure as a mean value of the second pressure and the third pressure; taking a mean value of the first target height difference and the second target height difference as a third target height difference;

determining the sample blood pressure information within the preset time period according to the fourth pressure and the third target height difference.

3. The method according to claim 2, wherein the step of determining the sample blood pressure information within the preset time period according to the fourth pressure and the third target height difference comprises:

acquiring a blood density of the target subject, determining a second blood static pressure at the first location according to the blood density and the third target height difference;

determining the sample blood pressure information within the preset time period according to the fourth pressure and the second blood static pressure.

4. The method according to claim 3, wherein the step of determining the sample blood pressure information within the preset time period according to the fourth pressure and the second blood static pressure comprises:

taking a sum of the fourth pressure and the second blood static pressure as the sample mean blood pressure;

determining an envelope of an oscillatory wave of the sample PPG signal at the first location;

determining a blood pressure at a third preset ratio of a rising edge of the envelope as a second SBP pressure;

taking a sum of the second SBP and the second blood static pressure as a sample SBP;

determining a blood pressure at a fourth preset ratio of a falling edge of the envelope as a second DBP; taking a sum of the second DBP and the second blood static pressure as a sample DBP.

5. The method according to claim 1, wherein the step of determining the TAG signals of the target subject according to the continuous target PPG signal and the plurality of beat-to-beat blood pressure information comprises:

determining a pre-established transfer function between the continuous target PPG signal and the plurality of beat-to-beat blood pressure information, inputting the plurality of beat-to-beat blood pressure information and the continuous target PPG signal into the transfer function, and obtaining the TAG signals output from the transfer function.

6. The method according to claim 1, wherein the step of determining the sample blood pressure information within each of the preset time periods according to the second pressure and the first target height difference comprises:

acquiring a blood density of the target subject, determining a first blood static pressure at the first location according to the blood density and the first target height difference;

determining the sample blood pressure information within each of the preset time periods according to the second pressure and the first blood static pressure.

7. The method according to claim 6, wherein the step of determining the sample blood pressure information within each of the preset time periods according to the second pressure and the first blood static pressure comprises:

taking a sum of the second pressure and the first blood static pressure as the sample mean blood pressure;

determining a blood pressure at a first preset ratio of a rising edge of the derivative as a first SBP; taking a sum of the first SBP and the first blood static pressure as the sample SBP;

determining a blood pressure at a second preset ratio of a falling edge of the derivative as a first DBP;

taking a sum of the first DBP and the first blood static blood pressure as the sample DBP.

8. The method according to claim 1, wherein the step of applying the first pressure at the first location comprises adjusting a diameter or a contract pressure of the ring-shaped device.

9. The method according to claim 1, wherein the ring-shaped device is worn at the first location; the first location being a distal end of a finger; the region of the body further comprises a second location, if the second location being a proximal end of the finger, a non-adjustable and PPG signal collectable ring-shaped device is worn at the second location; if the second location being other location not at a proximal end of the finger, a corresponding PPG signal collectable external electronic apparatus is worn at the second location.

10. The method according to claim 1, further comprises a filtering step of the sample PPG signal or the continuous target PPG signal:

acquiring an original PPG signal from a plurality of channels;

for the original PPG signal of any one of the channels, extracting a target component from the original PPG signal by integrating a constrained independent component analysis, an adaptive filtering, and a baseless source quantity assumption method, and inputting the target component into an adaptive filter to instruct the adaptive filter to perform recovery of the original PPG signal according to the target component.

11. The method according to claim 1, wherein after the step of determining TAG signals of the target subject according to the continuous target PPG signal and the beat-to-beat blood pressure information, further comprises:

transmitting the TAG signals to an external display apparatus to instruct the external display apparatus to display the TAG signals.

12. An electronic apparatus, comprising: a memory, a processor and a computer program stored in the memory, wherein the processor executes the computer program to implement the method steps of claim 1.

13. A calibration device of a blood pressure estimation model for determining TAG signals, comprising:

a device adapted to apply adjustable pressure for applying a pressure to a first location of a body of a target subject; wherein the device adapted to apply adjustable pressure comprises a ring-shaped device, a PTT determining module for determining a plurality of PTT of a plurality of respective pulse waves at respective moments of time at a region of the target subject's body during a movement within a plurality of preset time periods in response to a pressure applied at to a first location of the body;

wherein the first location is used as an initial location of the first location;

a sample blood pressure information determining module for performing a derivation for a curve composed of the plurality of respective PTT at the respective moment of time within each of the preset time period, determining a plurality of moments of time when a derivative satisfies a first condition as a plurality of first moments of time;

acquiring a first pressure at each of the first moment of time, acquiring a second pressure according to a distribution of the first pressure of all the first moments of time;

acquiring a first height difference of the first preset location at the first moment of time relative to a heart location;

obtaining a first target height difference according to a distribution of all the first height differences;

determining a sample blood pressure information within the preset time period according to the second pressure and the first target height difference;

the sample blood pressure information comprises at least one of a sample mean blood pressure, a sample SBP and a sample DBP;

a blood pressure estimation model obtaining module for performing calibration for a pre-established initial blood pressure estimation model indicating a relationship between a blood pressure information and a physiological signal based on the sample blood pressure information and a sample physiological signal of the plurality of preset time periods, and for obtaining a target blood pressure estimation model;

a beat-to-beat blood pressure information determining module for acquiring a continuous target physiological signal of the target subject at the first location, inputting the continuous target physiological signal to a pre-established target blood pressure estimation model to acquire a plurality of beat-to-beat blood pressure information output by the target blood pressure estimation model; wherein the continuous target physiological signal comprises a continuous target PPG signal;

a TAG signals determining module for determining TAG signals of the target subject according to the continuous target PPG signal and the beat-to-beat blood pressure information.

* * * * *